(12) United States Patent
Hagadorn

(10) Patent No.: US 7,910,760 B2
(45) Date of Patent: Mar. 22, 2011

(54) SEMI-RIGID LINKED DIAMINES, PRECURSORS THEREFOR, AND TRANSITION METAL DIAMIDO COMPLEXES AS CATALYSTS FOR OLEFIN POLYMERIZATION PROCESSES

(75) Inventor: John R. Hagadorn, Houston, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 311 days.

(21) Appl. No.: 12/103,355

(22) Filed: Apr. 15, 2008

(65) Prior Publication Data

US 2009/0259085 A1 Oct. 15, 2009

(51) Int. Cl.
*C07F 7/08* (2006.01)
*C07F 7/28* (2006.01)
(52) U.S. Cl. .................. 556/12; 549/212; 502/158
(58) Field of Classification Search ............ 556/12; 549/212; 502/158
See application file for complete search history.

(56) References Cited

U.S. PATENT DOCUMENTS 5,318,935 A 6/1994 Canich et al.
(Continued)

FOREIGN PATENT DOCUMENTS

EP 0 893 454 1/1999
(Continued)

OTHER PUBLICATIONS

Minglana et al., Coordinatively Unsaturated Ru(II) Species Ru(xantsil)(CO): A New Active Catalyst for Oligomerization/Deoligomerization of $HSiMe_2SiMe_3$ [xantsil = (9,9-Dimethylxanthene-4,5-diyl)bis(dimethylsilyl)]. Isolation of a Stabilized Form of the Silyl(silylene) Intermediates, Chemistry Letters, 2002, vol. 31, No. 3, pp. 406-407.

(Continued)

*Primary Examiner* — Porfirio Nazario Gonzalez

(57) ABSTRACT

The invention relates to a process for producing a complex for use in olefin polymerization and oligomerization of the general formula (III):

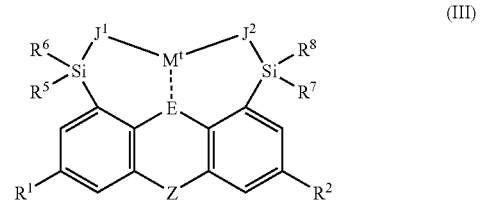

(III)

wherein $M^t$ is a group 3 to 12 element in a +2 to +6 oxidation state with between 1 to 4 additional ligands (anionic and/or neutral) coordinated, wherein $R^1$ and $R^2$ are hydrogen, halogen, alkoxy, or a hydrocarbon group containing between 1 to 12 carbon atoms; E is a group 16 element, preferably O; Z is a direct bond between carbon atoms of the adjacent aromatic rings or a $—CR^3R^4—$ or $—SiR^3R^4—$ bridge between those carbon atoms, where $R^3$ and $R^4$ are hydrogen or a hydrocarbon groups with 1 to 10 carbons, $R^5$, $R^6$, $R^7$ and $R^8$ are hydrogen, halogen, alkoxy, or a hydrocarbon group containing between 1 to 10 carbon atoms and $J^1$ and $J^2$ are $—NR^9R^{10}$ or $—PR^9R^{10}$, where $R^9$ is H or $SiMe_3$ group and $R^{10}$ is selected from a group consisting of alkyl, aryl, substituted aryl, heteroalkyl, and heteroaryl containing between 1 to 30 non-hydrogen atoms through a route involving novel precursors such as compounds represented by the general formula (I)

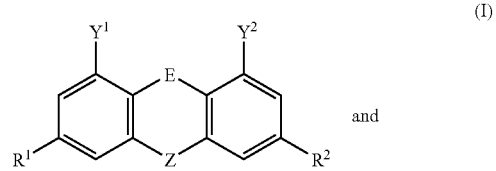

(I)

and

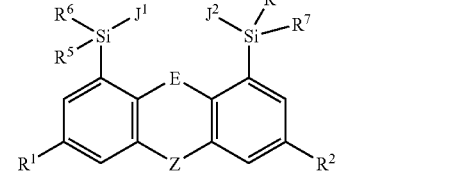

(II)

where the various substitution options are adapted to produce the substituents shown for formula (III) above.

11 Claims, 2 Drawing Sheets

U.S. PATENT DOCUMENTS

| | | | |
|---|---|---|---|
| 5,889,128 | A | 3/1999 | Schrock et al. |
| 6,271,325 | B1 | 8/2001 | McConville et al. |
| 6,656,868 | B2 | 12/2003 | Oskam et al. |
| 6,855,839 | B2 | 2/2005 | McConville et al. |
| 7,045,583 | B2 | 5/2006 | Kuchta et al. |

FOREIGN PATENT DOCUMENTS

| | | |
|---|---|---|
| WO | WO 98/46651 | 10/1998 |
| WO | WO 00/69922 | 11/2000 |
| WO | WO 01/26806 | 4/2001 |

OTHER PUBLICATIONS

Okazaki et al., Synthesis, structure, and reactivity of hydridobis-(silylene)ruthenium(IV)-xantsil complexes(silylene)ruthenium(IV)-xantsil complexes (xantsil = (9,9-dimethylxanthene-4,5-diyl)bis(dimethylsilyll)—A stabilized form of key intermediates in the catalytic oligomerization-deoligomerization of hydrosilanes[1], Canadian Journal of Chemistry, 2003, vol. 81, No. 11, pp. 1350-1358.

J.D. Scollard et al., "Living Polymerization of α-Olefins by Chelating Diamide Complexes of Titanium", J. Am. Chem. Soc., 1996, vol. 118, pp. 10008-10009.

J.D. Scollard et al., "Polymerization of α-Olefins by Chelating Diamide Complexes of Titanium", Macromolecules, 1996, vol. 29, pp. 5241-5243.

P. Mehrkhodavandi et al., "Living Polymerization of 1-Hexene by Cationic Zirconium and Hafnium Complexes that Contain a Diamido/Donor Ligand of the Type $[H_3CC(2-C_5H_4N)(CH_2NMNesityl)_2]^{2-}$. A Comparison of Methyl and Isobutyl Initiators", Organometallics, 2003, vol. 22, pp. 4569-4583.

LCLiang et al., Synthesis of Group 4 Complexes that Contain the Diamidoamine Ligands, $[(2,4,6-Me_3C_6H_2NCH_2CH_2)2NR]^{2-}$ $(([Mes_2N_2NR]^{2-}; R=H$ or $CH_3)$, and Polymerization of 1-Hexene by Activated $[Mes_2N_2NR]ZrMe_2$ Complexes, J. Am. Chem. Soc., 1999, vol. 121, pp. 5797-5798.

R. Baumann et al., "Synthesis of Titanium and Zirconium Complexes That Contain the Tridentate Diamido Ligand, $[((t\text{-}Bu\text{-}d_6)N\text{-}o\text{-}C_6H_4)_2O]^{2-}$ $(NON]^{2-})$ and the Living Polymerization of 1-Hexene by Activated $[NON]ZrMe_2$", J. Am. Chem. Soc., 1997, vol. 119, pp. 3830-3831.

R.R. Schrock et al., "Synthesis of Titanium, Zirconium, and Hafnium Complexes that Contain Diamido Donor Ligands of the Type $[(t\text{-}BuN\text{-}o\text{-}C_6H_4)2O]^{2-}$ and an Evaluation of Activated Versions for the Polymerization of 1-Hexene", Organometallics, 1999, vol. 18, pp. 3649-3670.

Miguel A. Flores et al., "Zirconium Complexes That Contain a Diamido O'Donor Ligand with a Restricted Geometry", Organometallics, 1999, vol. 18, pp. 3220-3227.

N.A.H. Male et al., Synthesis and structure of zirconium(IV) alkyl complexes with bi-, tri-, tetra- and penta-dentate amido ligands, J. Chem. Soc., Dalton Trans., 1997, pp. 2487-2494.

R.M. Porter et al., "Dimethylxanthene- and dibenzofuran-diamido complexes of titanium", Polyhedron, vol. 25, 2006, pp. 859-863.

SEMI-RIGID LINKED DIAMINES, PRECURSORS THEREFOR, AND TRANSITION METAL DIAMIDO COMPLEXES AS CATALYSTS FOR OLEFIN POLYMERIZATION PROCESSES

FIELD OF THE INVENTION

The invention relates to reactive intermediates for use especially but not exclusively in making polycyclic diamine ligand precursors. The invention further relates to transition metal complexes incorporating ligands derived from the precursors for use as catalysts in olefin polymerization and oligomerization processes. Specifically, this invention relates to reactive bi-functionalized intermediates, ligand precursors made using such intermediates, transition metal complexes incorporating bidentate ligands derived from such precursors and processes for making these; as well as olefin polymerization and oligomerization processes using such transition metal complexes as catalysts.

BACKGROUND OF INVENTION

Suitable transition metal complexes may be used in olefin oligomerization, involving the linking of a limited number of monomer units or in olefin polymerization wherein numerous monomer units are joined to form a polymer chain. The transition metal complexes are generally activated to perform their polymerization or oligomerization function. Activation involves, according to current theory, transformation of the neutral complex into a cation after interaction with a so-called activator.

U.S. Pat. No. 5,889,128 and WO 98/46651 describe catalysts systems suitable for living polymerizations at low temperatures (living polymerization requires the suppression of the chain termination reaction, which is most easily established at low temperatures). Polycyclic diamine ligand precursors are described in which phenyl groups are linked by a single atom oxygen bridge and nitrogen containing moieties are provided in the ortho position on the phenyl rings in which the nitrogen is directly linked to a carbon atom in the phenyl rings. In the transition metal complex the oxygen of the bridge is free to coordinate with the transition metal atom. The complex is used in conjunction with a non-coordinating anion activator, supplied in the form of the borane or a borate salt. Polymerization is started as low as −30° C.

It is among the objects of the invention to provide additional intermediates for the formation of improved ligands precursors that permit a broader range of transition-metal complexes for use in olefin polymerization. Among the objects is to provide more rigid structures with controlled amido-metal-amido angles; controlled dative interaction between a single hetero-bridging atom in the ligand and the transition metal, with improved performance at higher polymerization temperatures, especially in olefin polymerization and oligomerization, capable of providing a variety of molecular weights including an elevated molecular weight at elevated temperatures and with controlled incorporation of alpha-olefin monomers. It is furthermore among the objects to permit the synthesis of large, rigid steric ligands to reduce the symmetry of the transition metal complex and provide a bias towards stereoregular incorporation of higher alpha-olefins having at least three carbon atoms.

SUMMARY OF THE INVENTION

In a first aspect, the invention provides novel compounds for serving as an intermediate starting material in the formation of a neutral bidentate ancillary ligand precursor. Accordingly the invention firstly provides a compound represented by the general formula (I)

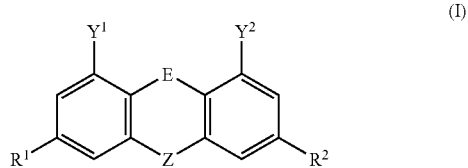

wherein $R^1$ and $R^2$ are hydrogen, halogen, alkoxy or a hydrocarbon group containing between 1 to 10 carbon atoms; E is a group 16 element, preferably O; Z is a direct bond between carbon atoms of the adjacent aromatic rings or a —$CR^3R^4$— or —$SiR^3R^4$— bridge between those carbon atoms, where $R^3$ and $R^4$ are hydrogen or a hydrocarbon groups with 1 to 10 carbons, and $Y^1$ and $Y^2$ are halosilyl groups. Where E is oxygen and Z is a direct bond between carbon atoms of the adjacent aromatic rings, the compound is a dibenzofuran derivative. Where E is oxygen and Z is a —$CR^3R^4$— bridge between those carbon atoms, it is a xanthene derivative. Xanthene and dibenzofuran compounds are preferred.

The compounds may be synthesized by a process which comprises coupling a 4,5-dilithio compound with a —$CR^3R^4$— or —$SiR^3R^4$— bridge between adjacent aromatic rings in the 9 position xanthene derivative or a 4,6-dilithio compound with a direct bond between carbon atoms of the adjacent aromatic rings with a dihalosilane so as to produce the compound represented by the formula (I). Preferably the process comprises coupling a 4,5-dilithioxanthene derivative or a 4,6-dilithiodibenzofuran derivative with a dihalosilane to produce the corresponding xanthene or dibenzofurane derivative.

In a second aspect the invention provides novel neutral, diamine ligand precursors, with multi-ring rigid linker groups connecting the individual amine moieties that may be used in the synthesis of transition metal complexes. In this aspect the invention provides a compound for use as a ligand in a transition metal complex represented by the general formula (II):

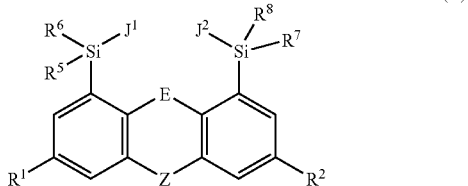

wherein $R^1$ and $R^2$ are hydrogen, halogen, alkoxy, or a hydrocarbon group containing between 1 to 10 carbon atoms; E is a group 16 element, preferably O; Z is a direct bond between carbon atoms of the adjacent aromatic rings or a —$CR^3R^4$— or —$SiR^3R^4$— bridge between those carbon atoms, where $R^3$ and $R^4$ are hydrogen or a hydrocarbon groups with 1 to 10 carbons, $R^5$, $R^6$, $R^7$ and $R^8$ are hydrogen, halogen, alkoxy or a hydrocarbon group containing between 1 to 12 carbon atoms, and $J^1$ and $J^2$ are —$NR^9R^{10}$ or —$PR^9R^{10}$, where $R^9$ is a H or $SiMe_3$ group and $R^{10}$ is selected from a group consisting of alkyl, aryl, substituted aryl, heteroalkyl, and heteroaryl containing between 1 to 30 non-hydrogen atoms. Me is methyl.

The diamine ligand precursor may be prepared by a process which comprises reacting the compound represented by the formula (I) with an amine or a group 1 or 2 metal amide to form a ligand precursor compound represented by the formula (II).

These precursors can be used to form ligands in transition-metal complexes which, when activated, react with alkenes to form polymers and oligomers. Thus in a third aspect of the invention there is provided a transition metal complex of the general formula (II):

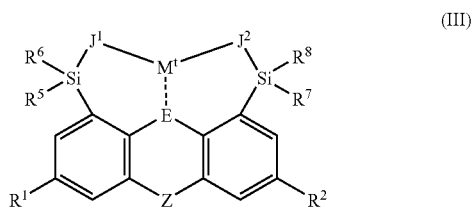

(III)

wherein $M^t$ is a group 3 to 12 element in a +2 to +6 oxidation state (such as +2, +3, +4, +5 or +6) with between 1 to 4 additional ligands (anionic and/or neutral) coordinated, wherein $R^1$ and $R^2$ are hydrogen, halogen, alkoxy, or a hydrocarbon group containing between 1 to 12 carbon atoms; E is a group 16 element, preferably O; Z is a direct bond between carbon atoms of the adjacent aromatic rings or a —$CR^3R^4$— or —$SiR^3R^4$— bridge between those carbon atoms, where $R^3$ and $R^4$ are hydrogen or a hydrocarbon groups with 1 to 10 carbons, $R^5$, $R^6$, $R^7$ and $R^8$ are hydrogen, halogen, alkoxy, or a hydrocarbon group containing between 1 to 10 carbon atoms and $J^1$ and $J^2$ are —$NR^9R^{10}$ or —$PR^9R^{10}$, where $R^9$ is H or $SiMe_3$ group and $R^{10}$ is selected from a group consisting of alkyl, aryl, substituted aryl, heteroalkyl, and heteroaryl containing between 1 to 30 non-hydrogen atoms. Me is methyl.

The transition metal complexes may be synthesized by a process which comprises subjecting the compound represented by the formula (II) to deprotonation by a group 1 or 2 organometallic base followed by reaction of the generated metal amide with a transition metal halide to produce a transition metal complex represented by the formula (III).

In yet a further aspect of the invention, the complex may be used to form a catalysts system for polymerization. These complexes, in combination with appropriate activators, have activity as catalysts for olefin polymerization such as ethylene based polymers or propylene based polymers, including ethylene-octene polymerization. The catalyst systems may be used in polymerization or oligomerization process involving the contacting an olefin monomer with the catalyst system in which the $M^t$ is selected from a group 4 transition metal (such as Ti, Zr of Hf). Suitably the catalyst system comprises the reaction product of a complex of the formula (III), and an activator selected from the group consisting of alumoxanes and non-coordinating anion activators.

DETAILED DESCRIPTION OF THE INVENTION

Figure 1:
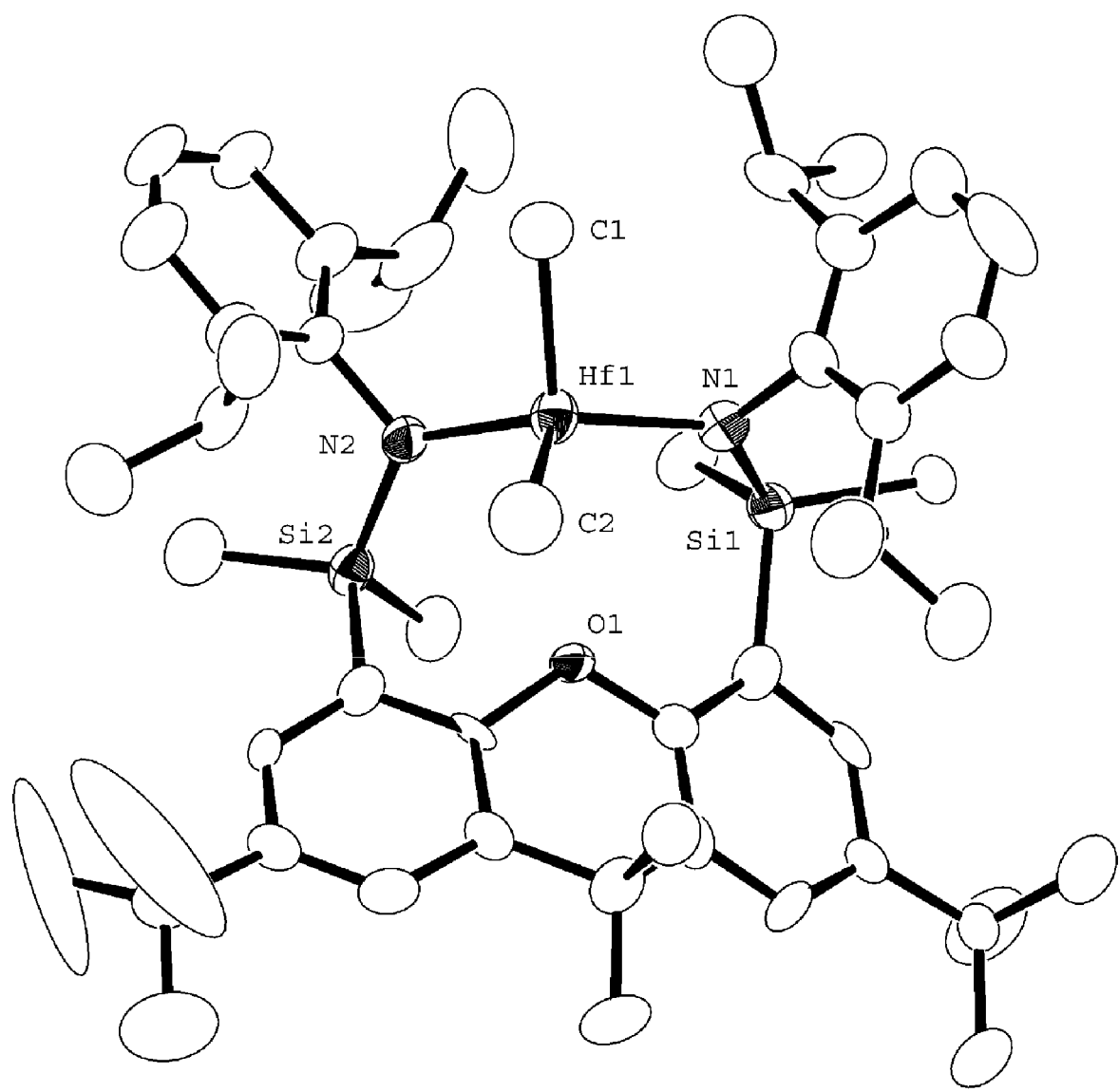
FIG. 1 is an illustration of the molecular structure of [2a]$HfMe_2$ compound drawn with 50% thermal ellipsoids as determined by single-crystal X-ray diffraction.

The specification describes transition metal complexes. The metal of the complex is coordinated to an ancillary ligand that is bulky and stably bonded to the transition metal. The ligand is derived from a neutral ligand precursor. The ligand may be coordinated to the transition metal by covalent bond and/or electron donation coordination.

In the specification and claims groups are referred to as "reactive". By the term "reactive" is meant that the group may be used to couple the compound to other compounds in chemical reactions, and is used in this case mainly to indicate the suitability for reacting in a substitution reaction to form a diamine ligand precursor.

The standard numbering schemes for xanthene and dibenzofuran are shown below. These numbering schemes are used in the description of the compounds herein.

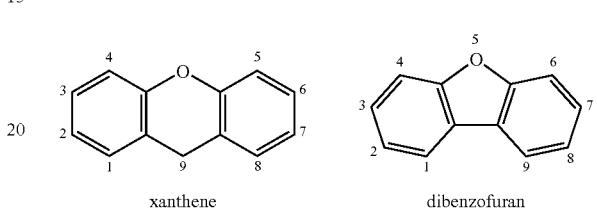

xanthene                dibenzofuran

In the specification and claims moieties and/or substituents may be the same or different unless otherwise mentioned. For example the —$NR^1R^2$ group described wherein $R^1$ and $R^2$ may be an alkyl group or an alkoxy group having from 3 to 10 carbon atoms, is to be construed as signifying that the individual groups may at the same time include a $C_3$ and $C_{10}$ moiety or an alkyl and an alkoxy. The same numbering system is used for other compounds in which the carbon at the 9-position in xanthene is replaced by a silicon atom and/or where the oxygen atom is replaced by another group 16 element.

In a preferred embodiment, a new class of diamine ligand precursors featuring rigid linker groups have been prepared and used to form diamido transition-metal derivatives is disclosed herein. Diamido Zr and Hf derivatives, when activated, have been found to polymerize or oligomerize alkenes.

The invention provides precursors of the diamines having multi-ring linker groups. The linker groups may be based on xanthene and dibenzofuran frameworks. While in both cases a single oxygen atom bridges two aromatic rings which are held firmly in position due to the additional link between facing carbon atoms of the aromatic rings, the shape of the ligand and the manner of the steric environment around the transition metal atom will differ.

The two amine functionalities of the diamine ligand precursors are joined by a tricyclic linker that may be a 4,5-amine disubstituted 2,7-di-tert-butyl-9,9-dimethylxanthene (wherein $R^3$ and $R^4$ in —$CR^3R^4$— in formula (II) are both methyl) or a 4,6-amine disubstituted dibenzofuran. The xanthene and dibenzofuran linkers may be further substituted as shown in formula (II) and particularized in the examples below. The amine groups are joined to the linkers through silyl bridging groups. The diamines can be used to prepare diamido derivatives wherein $M^t$ is Zr or Hf, which are useful as catalysts, when activated, for alkene oligomerization and polymerization reactions. In these catalytic applications the xanthene linker unit is preferred. The amines each may feature an alkyl, aryl, or substituted aryl group. Substitution of these aryl groups in the ortho positions (i.e., 2,6-disubstituted aryls) is preferred for the formation of high molecular weight polyolefins. 2,6-Diethylphenyl groups are much preferred.

The formation of chiral diamine ligand precursors may be accomplished through the use of unsymmetrically substituted silyl groups, —SiR$^a$R$^b$— (R$^a$ not equal to R$^b$, where R$^a$ and R$^b$ are selected from the group consisting of hydrogen, halogen, alkoxy, or a hydrocarbon group containing between 1 to 10 carbon atoms), which join the tricyclic linker to the amine groups. Either $C_1$- or $C_2$-symmetric diamines can be accessed by this method depending upon whether one or two unsymmetrically substituted silyl group is used. A similar approach can be used for the carbon analogues, wherein the Si atom is replaced by a carbon. The use of these diamines to form chiral diamido metal derivatives is of interest for the formation of catalysts that, when activated, are useful for producing stereoregular poly (alpha olefins), especially isotactic polypropylene.

Examples of these linked diamine ligand precursors of the invention and their abbreviations are shown below:

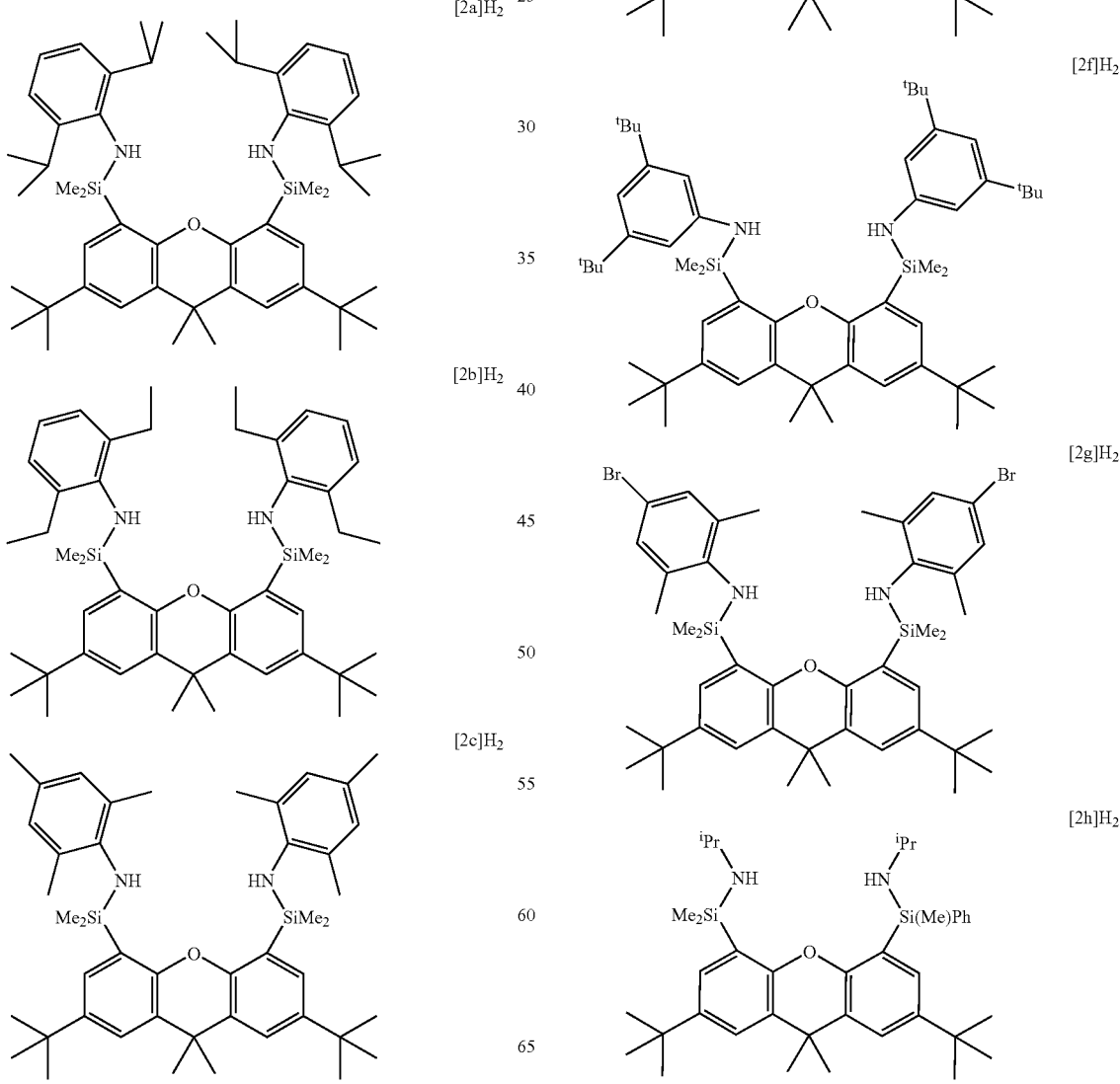

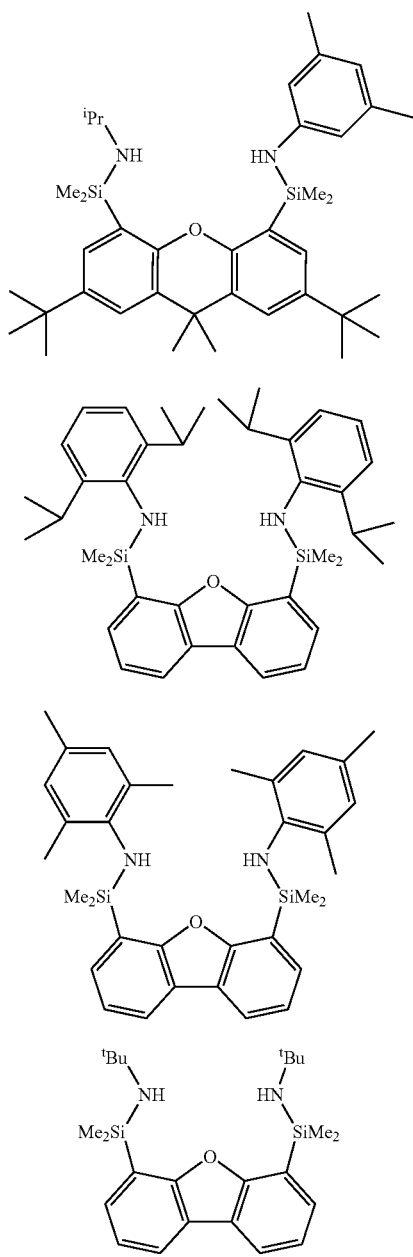

where Me is methyl, ⁱbu is tertiary butyl, and ⁱPr is isopropyl.

The first type of linked diamine ligand precursor has a 4,5-disubstituted xanthene backbone and is exemplified by diamine [2a]H₂ (this particular diamine is also substituted in the 2 and 7 positions with tert-butyl groups). The second type of linker features a 4,6-disubstituted dibenzofuran. This type of linker is used in ligand [4a]H₂, for example.

Synthesis of all of the aforementioned linked diamines is from known lithio derivatives. In particular these may be variously substituted 4,5-dilithioxanthenes and 4,6-dilithiodibenzofurans.

The dilithio derivatives can be prepared by various methods. One convenient method is the lithium-halogen exchange reaction between an appropriate dihalo derivative (e.g., 4,6-diiododibenzofuran, 4,5-dibromo-2,7-di(tert-butyl)-9,9-dimethylxanthene) and an alkyl lithium (e.g., butyllithium). Suitable dihalo derivatives include xanthenes substituted in the 4 and 5 positions with bromine, iodine, and triflate groups. Suitable dihalo derivatives also include dibenzofurans substituted in the 4 and 6 positions with bromine, iodine, and triflate groups.

A second method for the preparation of the dilithio derivatives is by the direct deprotonation of xanthenes that are unsubstituted in the 4 and 5 positions with strong organolithium bases, such as n-BuLi/TMEDA (n-bu is n-butyl, TMEDA=N, N, N',N'-tetramethylethylenediamine) or sec-BuLi. This method can also be applied for the preparation of dilithio derivatives of dibenzofuran by the direct deprotonation of dibenzofurans that are unsubstituted in the 4 and 6 positions by deprotonation with strong organolithium bases, such as n-BuLi/TMEDA or sec-BuLi. From these known lithio reagents novel, reactive halosilyl derivatives of the invention may be prepared e.g., by reaction with the dialkyl dihalosilanes. These may feature chlorosilane groups directly joined to the linkers. Examples of reactive halosilyl derivatives include 4,5-bis(chlorodimethylsilyl)-2,7-di(tert-butyl)-9,9-dimethylxanthene and 4,6-bis(chlorodimethylsilyl) dibenzofuran. The chlorosilane intermediates may be reacted with either metal amides or amines to form the linked diamine ligand precursors.

The linked diamines can be doubly deprotonated to form diamidos, which are also called diamides. Thus the double deprotonation of diamine [2a]H₂ will form the dianion [2a]²⁻, which in formula abbreviations for transition metal complexes (see below) is also indicated by simply [2a]. The diamidos bind to transition metals as ligands to form diamido complexes. Representative examples of these complexes are shown below.

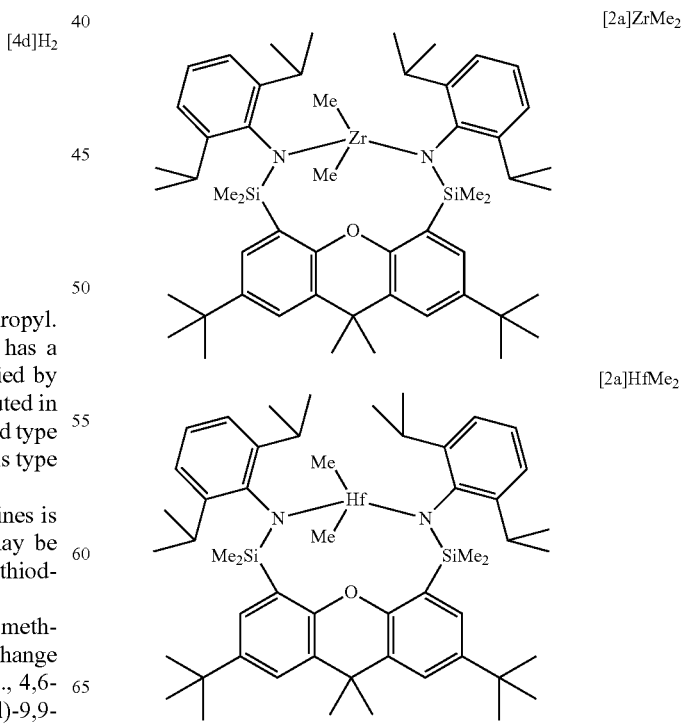

-continued
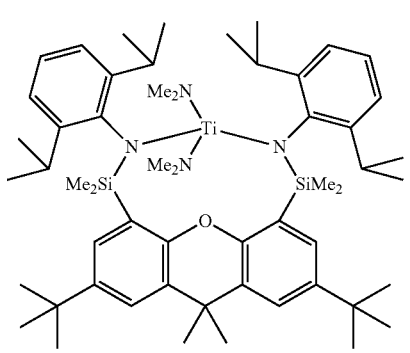
[2a]Ti(NMe₂)₂
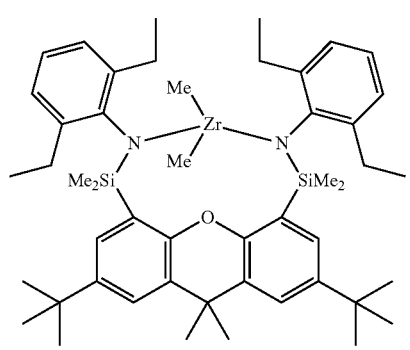
[2b]ZrMe₂
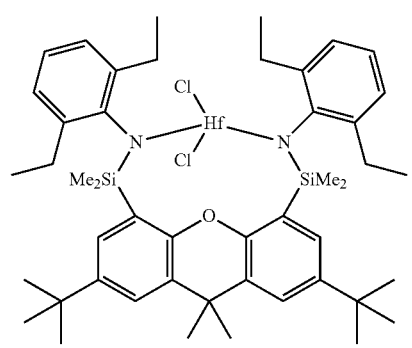
[2b]HfCl₂
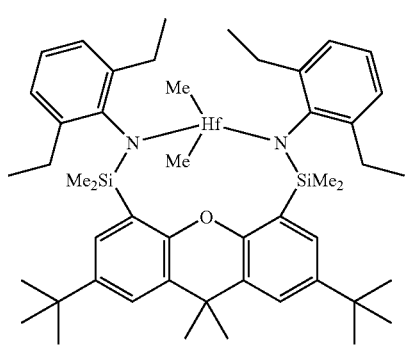
[2b]HfMe₂
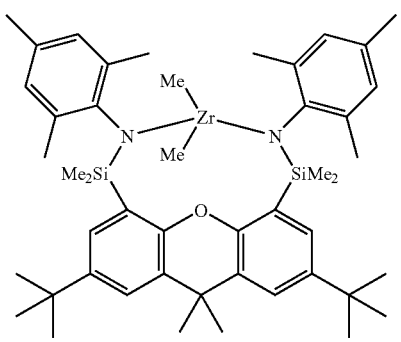
[2c]ZrMe₂
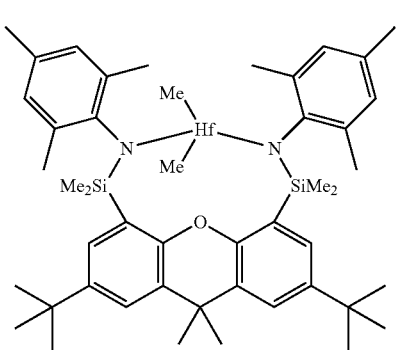
[2c]HfMe₂
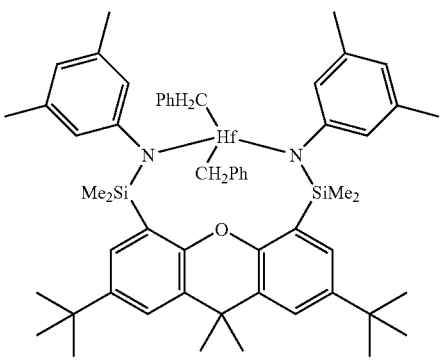
[2e]HfBn₂
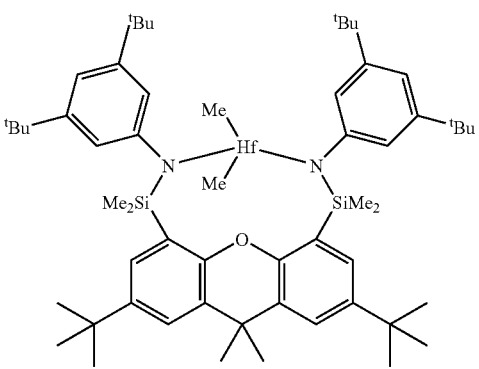
[2f]HfMe₂

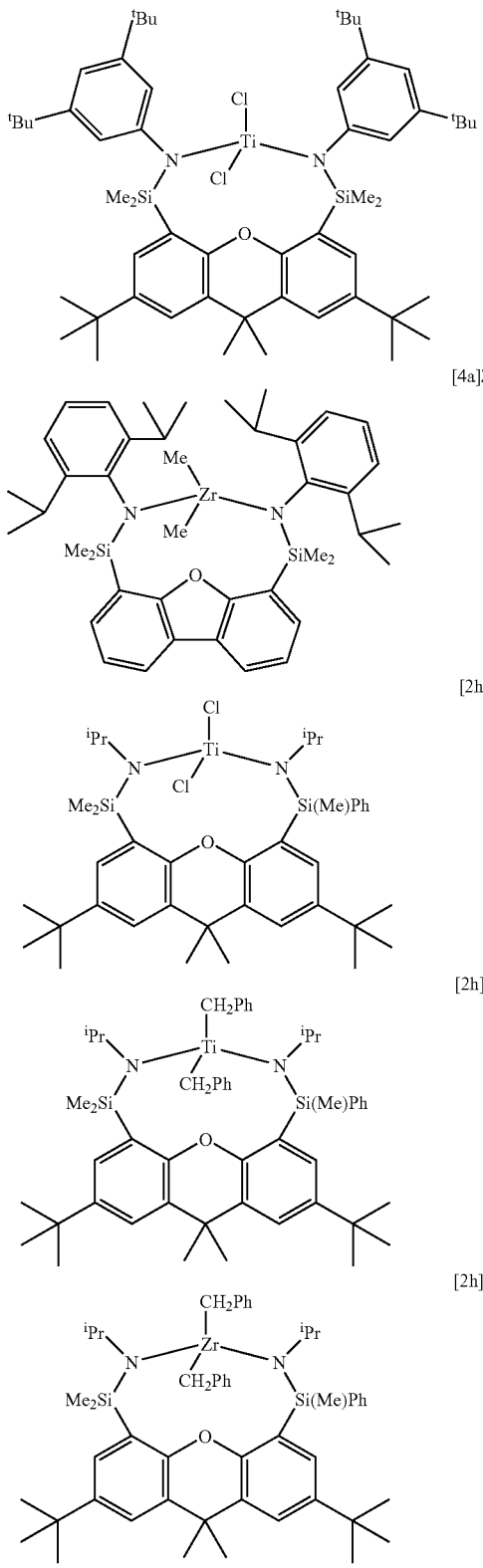

where Me is methyl, Ph is phenyl, $^i$Pr is isopropyl, and $^t$Bu is t-butyl and Bn is benzyl.

The linked diamines can be doubly deprotonated to form diamidos, which are also called diamides. Thus the double deprotonation of diamine [2a]H$_2$ will form the dianion [2a]$^{2-}$, which in formula abbreviations for transition metal complexes (see below) is also indicated by simply [2a]. The diamidos bind to transition metals as ligands to form diamido complexes. Representative examples of these complexes are shown below.

The transition metal diamido complexes are typically prepared by any of three different methods. The first can be called a protonolysis reaction. Typically, in this protonolysis reaction a diamine ligand precursor is reacted with a known organometallic or metal(amido) reagent. Some examples of these reagents include TiBn$_4$, ZrBn$_4$, HfBn$_4$, ZrBn$_2$Cl$_2$(OEt$_2$), HfBn$_2$Cl$_2$(OEt$_2$), Ti(NMe$_2$)$_4$, Zr(NMe$_2$)$_4$, Hf(NMe$_2$)$_4$ and Ti(NMe$_2$)$_2$Cl$_2$, where Et is ethyl, Bn is benzyl, and Me is methyl. If desired, the product of this protonolysis reaction can be subsequently alkylated using an alkylating reagent such Me$_3$Al or Me$_2$Mg or MeLi (where Me is methyl) or other common organometallic reagents.

The second method is a salt-metathesis reaction. Typically, in this salt-metathesis reaction a di(lithioamido) species is reacted with a transition metal halide, such as ZrCl$_4$, ZrCl$_4$(thf)$_2$, HfCl$_4$, HfCl$_4$(thf), Ti(NMe$_2$)$_2$Cl$_2$, ZrBn$_2$Cl$_2$(OEt$_2$), or HfBn$_2$Cl$_2$(OEt$_2$), where thf is tetrahydrofuran, Me is methyl, Bn is benzyl, and Et is ethyl. This reaction forms the diamido complex and a byproduct salt, typically LiCl.

A third method for the formation of the diamido complexes involves the reaction of a silylated diamine with a metal halide, such as TiCl$_4$ or ZrCl$_4$. The products of such a reaction are the diamido complex and a chlorosilane. This method would require the conversion of a diamine ligand precursor, such as [4a]H$_2$, to its silylated derivative. This is typically accomplished by deprotonation of the diamine followed by reaction with Me$_3$SiCl (Me is methyl) to form the silylated derivative and a byproduct salt.

Depending on the metal component used to prepare the transition metal complex lignds may be attached as what are generally referred to as "leaving groups", presumed detached or detachable to form the cationic active catalysts species in the presence of a suitable activator such a Cl, Me, etc.

After the complexes have been synthesized, catalyst systems may be formed by combining them with activators in any of the methods known from the literature including by supporting them for use in slurry or gas phase polymerization or an oligomerization process. Oligomerization is defined herein as the combination of from 2 to 5 monomer units. This may be achieved while leaving terminal unsaturation so that the resulting oligomers can if desired take part in subsequent polymerization as a monomer. Polymerization is defined herein as the combination of sufficient monomer units to provide a number average molecular weight of at least 2000 g/mol as determined by GPC DRI.

The catalyst systems may also be added to or generated in solution polymerization or bulk polymerization (in the monomer). In the polymerization and oligomerization processes of this invention, Zr and Hf derivatives are preferred although Ti may also be found useful. The complexes are activated towards alkene polymerization by reaction with non-coordinating anions (such as either N,N-dimethylanilinium tetrakis (pentafluorophenyl)borate) or with alumoxanes (such as methyl alumoxane or similar modified materials, designated as MAO), to form activated species. The activated species react with alkenes to form oligomers or polymers. The catalysts system and/or its individual components may be supported on conventional carrier materials such as silica or micro porous clays.

The use of non-coordinating anion activators, such as N,N-dimethylanilinium tetrakis(pentafluorophenyl)borate, is preferred over alumoxanes for the formation of high molecular weight polymers. Hf is preferred to Zr for the formation of catalysts that operate at higher temperatures to produce high molecular weight polyolefins.

Activation may be performed using alumoxane solution supplied by Albemarle including methyl alumoxane, referred to as MAO, as well as modified MAO, referred to herein as MMAO, containing some higher alkyl groups to improve the solubility. MAO can be purchased from Albemarle in a 10 wt % solution in toluene.

Activation may also be performed using non-coordinating anions, referred to as NCAs, of the type described in EP 277 003 A1 and EP 277 004 A1. NCAs may be added in the form of an ion pair using, for example, [DMAH]$^+$[NCA]$^-$ in which the N,N-dimethylanilinium (DMAH) cation reacts with a basic leaving group on the transition metal complex to form a transition metal complex cation and [NCA]$^-$. The cation in the precursor may, alternatively, be trityl. Alternatively, the transition metal complex may be reacted with a neutral NCA precursor, such as B(C$_6$F$_5$)$_3$, which abstracts an anionic group from the complex to form an activated species. Useful activators include N,N-dimethylanilinium tetrakis(pentafluorophenyl)borate (i.e., [PhNMe$_2$H]B(C$_6$F$_5$)$_4$) and N,N-dimethylanilinium tetrakis(heptafluoronaphthyl)borate, where Ph is phenyl, and Me is methyl. Typically, the activator and metal compound are combined at molar ratios of to 1:1 to 100:1, alternately 1:1 to 10:1, preferably 0.5 to 1 to 2:1 where the activator is an NCA and at ratios of 1:1 to 50,000:1, alternately 1:1 to 25,000:1, alternately 1:1 to 1000:1 where the activator is an alumoxane.

Polymerization may be homogeneous (solution or bulk polymerization) or heterogeneous (slurry in a liquid diluent) or gas phase (in a gaseous diluent). The polymerization is preferably continuous and uses an appropriately formulated catalyst system employing the transition metal complex. In the case of heterogeneous slurry or gas phase polymerization, the complex and activator may be supported by conventional methods. Silica is useful as a support herein.

Monomers useful herein include olefins having from 2 to 20 carbon atoms, alternately 2 to 10 carbon atoms (preferably ethylene, propylene, butene, pentene, hexene, heptene, octene, nonene, decene, and dodecene) and optionally also polyenes (such as dienes, e.g., cyclopentadiene, 1,5-hexadiene, etc.). Where olefins are used that give rise to short chain branching, such as propylene, the catalyst systems may, under appropriate conditions, generate stereoregular polymers or polymers having stereoregular sequences in the polymer chains. Particularly preferred monomers include ethylene, and mixtures of C$_2$ to C$_{10}$ alpha olefins, such as ethylene-propylene, ethylene-hexene, ethylene-octene, propylene-hexene, and the like.

In another embodiment, this invention relates to:
1. A compound represented by the general formula (I)

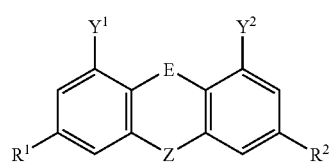

(I)

wherein R$^1$ and R$^2$ are hydrogen, halogen, alkoxy or a hydrocarbon group containing between 1 to 10 carbon atoms; E is a group 16 element, preferably O; Z is a direct bond between carbon atoms of the adjacent aromatic rings or a —CR$^3$R$^4$— or —SiR$^3$R$^4$— bridge between those carbon atoms, where R$^3$ and R$^4$ are hydrogen or a hydrocarbon groups with 1 to 10 carbons, and Y$^1$ and Y$^2$ are halosilyl groups.

2. A compound for use as a ligand in a transition metal complex represented by the general formula (II):

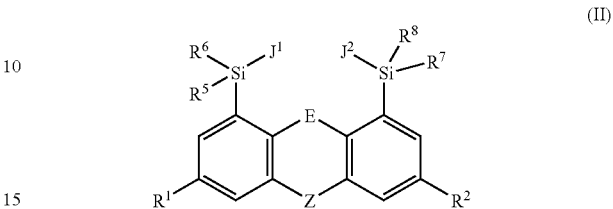

(II)

wherein R$^1$ and R$^2$ are hydrogen, halogen, alkoxy, or a hydrocarbon group containing between 1 to 10 carbon atoms; E is a group 16 element, preferably O; Z is a direct bond between carbon atoms of the adjacent aromatic rings or a —CR$^3$R$^4$— or —SiR$^3$R$^4$— bridge between those carbon atoms, where R$^3$ and R$^4$ are hydrogen or a hydrocarbon groups with 1 to 10 carbons, R$^5$, R$^6$, R$^7$ and R$^8$ are hydrogen, halogen, alkoxy or a hydrocarbon group containing between 1 to 12 carbon atoms and J$^1$ and J$^2$ are —NR$^9$R$^{10}$ or —PR$^9$R$^{10}$, where R$^9$ is a H or SiMe$_3$ group and R$^{10}$ is selected from a group consisting of alkyl, aryl, substituted aryl, heteroalkyl, and heteroaryl containing between 1 to 30 non-hydrogen atoms.

3. A transition metal complex of the general formula (III):

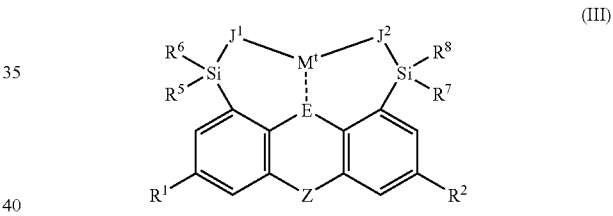

(III)

wherein M' is a group 3 to 12 element in a +2 to +6 oxidation state (preferably +2, +3, +4, +5 or +6) with between 1 to 4 additional ligands (anionic and/or neutral) coordinated, wherein R$^1$ and R$^2$ are hydrogen, halogen, alkoxy, or a hydrocarbon group containing between 1 to 12 carbon atoms; E is a group 16 element, preferably O; Z is a direct bond between carbon atoms of the adjacent aromatic rings or a —CR$^3$R$^4$— or —SiR$^3$R$^4$— bridge between those carbon atoms, where R$^3$ and R$^4$ are hydrogen or a hydrocarbon groups with 1 to 10 carbons, R$^5$, R$^6$, R$^7$ and R$^8$ are hydrogen, halogen, alkoxy, or a hydrocarbon group containing between 1 to 10 carbon atoms and J$^1$ and J$^2$ are —NR$^9$R$^{10}$ or —PR$^9$R$^{10}$, where R$^9$ is H or SiMe$_3$ group and R$^{10}$ is selected from a group consisting of alkyl, aryl, substituted aryl, heteroalkyl, and heteroaryl containing between 1 to 30 non-hydrogen atoms.

4. The transition metal complex according to paragraph 3 in which the two amine functionalities of the diamine ligand precursor are joined by a tricyclic linker that may be either a 4,5-disubstituted 9,9-dimethylxanthene or a 4,6-disubstituted dibenzofuran.

5. The transition metal complex according to paragraph 3 or paragraph 4 in which R$^{10}$ is an aryl moiety substituted in the ortho positions, such as, i.e., 2,6-disubstituted aryl moieties.

6. The transition metal complex according to any of paragraphs 3 to 5 in which R$^{10}$ contains 2,6-diethylphenyl moieties.

7. A process for producing a halosilane intermediate for a ligand precursor according to claim 1 which comprises coupling a 4,5-dilithioxanthene derivative or a 4,6-dilithiodibenzofuran derivative with a dihalosilane and producing a compound represented by the formula (I):

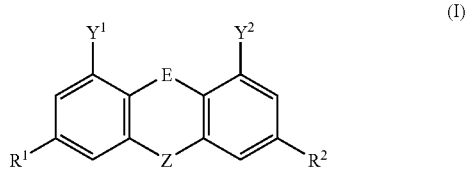
(I)

wherein $R^1$ and $R^2$ are hydrogen, halogen, alkoxy or a hydrocarbon group containing between 1 to 10 carbon atoms; E is O; Z is a direct bond between carbon atoms of the adjacent aromatic rings or a —$CR^3R^4$— bridge between those carbon atoms, where $R^3$ and $R^4$ are hydrogen or a hydrocarbon groups with 1 to 10 carbons, and $Y^1$ and $Y^2$ are reactive halosilyl groups 8. The process according to paragraph 7 further comprising reacting the compound represented by the formula (I) with an amine or a group 1 or 2 metal amide to form a ligand precursor compound represented by the formula (II):

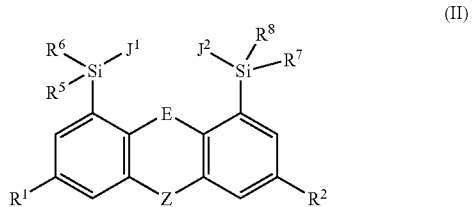
(II)

wherein $R^1$ and $R^2$ are hydrogen, halogen, alkoxy, or a hydrocarbon group containing between 1 to 10 carbon atoms; E is a group 16 element, preferably O; Z is a direct bond between carbon atoms of the adjacent aromatic rings or a —$CR^3R^4$— or —$SiR^3R^4$— bridge between those carbon atoms, where $R^3$ and $R^4$ are hydrogen or a hydrocarbon groups with 1 to 10 carbons, $R^5$, $R^6$, $R^7$ and $R^8$ are hydrogen, halogen, alkoxy or a hydrocarbon group containing between 1 to 12 carbon atoms and $J^1$ and $J^2$ are —$NR^9R^{10}$ or —$PR^9R^{10}$, where $R^9$ is a H or $SiMe_3$ group and $R^{10}$ is selected from a group consisting of alkyl, aryl, substituted aryl, heteroalkyl, and heteroaryl containing between 1 to 30 non-hydrogen atoms.

9. The process according to paragraph 8 which comprises subjecting the compound represented by the formula (II) to deprotonation by a group 1 or 2 organometallic base followed by reaction of the generated metal amide with a transition metal halide to produce a transition metal complex represented by the formula (III):

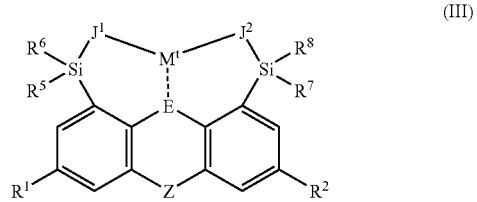
(III)

wherein $M^t$ is a group 3 to 12 element in a +2 to +6 oxidation state (such as +2, +3, +4, +5 or +6) with between 1 to 4 additional ligands (anionic and/or neutral) coordinated, wherein $R^1$ and $R^2$ are hydrogen, halogen, alkoxy, or a hydrocarbon group containing between 1 to 12 carbon atoms; E is a group 16 element, preferably O; Z is a direct bond between carbon atoms of the adjacent aromatic rings or a —$CR^3R^4$— or —$SiR^3R^4$— bridge between those carbon atoms, where $R^3$ and $R^4$ are hydrogen or a hydrocarbon groups with 1 to 10 carbons, $R^5$, $R^6$, $R^7$ and $R^8$ are hydrogen, halogen, alkoxy, or a hydrocarbon group containing between 1 to 10 carbon atoms and $J^1$ and $J^2$ are —$NR^9R^{10}$ or —$PR^9R^{10}$, where $R^9$ is H or $SiMe_3$ group and $R^{10}$ is selected from a group consisting of alkyl, aryl, substituted aryl, heteroalkyl, and heteroaryl containing between 1 to 30 non-hydrogen atoms.

10. A catalyst system comprising the reaction product of a complex according to any of paragraphs 3 to 6, and an activator selected from the group consisting of alumoxanes and non-coordinating anion activators.

11. A catalyst system according to paragraph 10, in which the activator comprises a salt of a cation and an $[B(C_6F_5)_4,]$ or $[B(C_{10}F_7)_4,]$ anion.

12. A polymerization or oligomerization process which comprises contacting an olefin monomer with the catalyst system of claim 10 or claim 11 in which the Mt is selected from group 4 transition metals (preferably Hf, Zr and Ti, preferably Hf and Zr).

13. The polymerization or oligomerization process according to paragraph 12 in which the catalyst system includes a Zr or Hf diamido derivative of a xanthene-linked ligand precursor and the monomer is an alkene.

14. The polymerization process according to paragraph 13 in which the polymerization temperature is at least 50° C., the transition metal complex is a hafnium complex and the activator is a non-coordinating anion.

EXAMPLES

Abbreviations used herein include: Et is ethyl, Bu is butyl, Me is methyl, tBu is tertiary-butyl, thf is tetrahydrofuran, TMEDA is N, N, N', N'-tetramethylethylenediamine, Bn is benzyl, and Ph is phenyl.

Example 1

Synthesis of 4,5-bis(chlorodimethylsilyl)-2,7-di(tert-butyl)-9,9-dimethylxanthene (1)

The reaction outlined in the reaction scheme below is as follows: $Et_2O$ (125 mL) and 4,5-dibromo-2,7-di(tert-butyl)-9,9-dimethylxanthene (9.54 g, 19.9 mmol) were combined and cooled to −65° C. A hexane solution of BuLi (19.2 mL, 47.7 mmol) was added dropwise over 5 min and the colorless suspension was allowed to warm to −30° C. over a period of 45 min during which time the starting material dissolved (at about −40° C.). After 15 min at −30° C. the solution was cooled to −80° C. and cold $SiMe_2Cl_2$ (20.5 g, 159 mmol) was added in one portion.

The mixture was allowed to warm to ambient temperature out of the cold bath. Colorless precipitate formed. Volatiles were then removed under reduced pressure and the white solid was extracted with $CH_2Cl_2$ (50 mL) and filtered. The volatiles were removed to afford a sticky white solid. This was suspended in hot hexane (30 mL) briefly then the mixture was cooled to −35° C. for 2 h. The white solid was then collected on a glass frit and washed with hexane.

The white 4,5-bis(chlorodimethylsilyl)-2,7-di(tert-butyl)-9,9-dimethylxanthene was dried under reduced pressure. Yield: 8.40 g, 83.1%. $^1$H NMR ($C_6D_6$): δ 7.96 (2H, d), 7.57 (2H, d), 1.55 (6H, s), 1.30 (18H, s), 0.82 (12H, s).

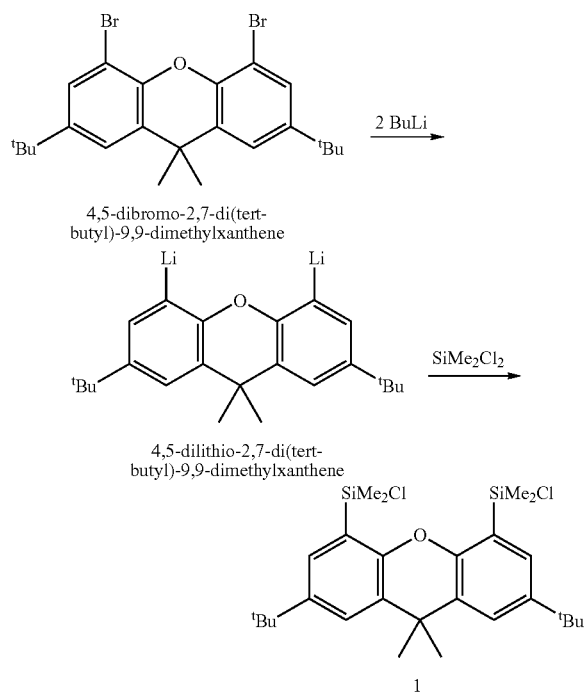

Example 2

Synthesis of [2b]H$_2$

The reaction outlined in the reaction scheme below is as follows: Benzene (7 mL) was added to the product 1 produced by the preceding reaction scheme (0.484 g, 0.954 mmol) and 2,6-diethylanilidolithium (0.296 g, 1.91 mmol) to form a pale yellow suspension. A few drops of tetrahydrofuran (thf) were then added to form a homogeneous solution from which some fine colorless precipitate, presumably LiCl, formed. After 20 min the volatiles were removed and the residue was extracted with hexane (5 mL).

Filtration and removal of the volatiles afforded clean [2b]H$_2$ as a microcrystalline solid. Yield: 0.696 g, 99.5%. $^1$H NMR ($C_6D_6$): δ 7.62 (4H, s), 6.95-6.87 (6H, m), 3.98 (2H, s), 2.55 (8H, q), 1.73 (6H, s), 1.35 (18H, s), 1.02 (12H, t), 1.62 (12H, s).

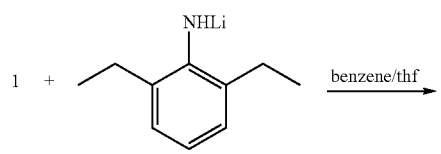

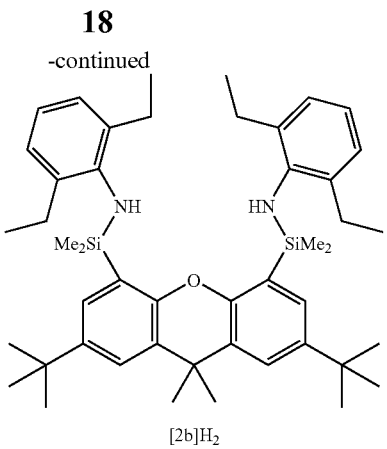

[2b]H$_2$

Example 3

Synthesis of [2c]H$_2$

Toluene (25 mL) was added to the product 1 produced by the preceding reaction scheme (2.696 g, 5.310 mmol) and 2,4,6-trimethylanilidolithium (1.499 g, 10.62 mmol) to form a pale yellow suspension. Then a few drops of tetrahydrofuran were added to form a homogeneous solution from which some fine precipitate formed. After 30 min the volatiles were removed and the oily residue was extracted with Et$_2$O (15 mL). Filtration and removal of the volatiles afforded the product as an oil that subsequently crystallized. Yield: 3.79 g, 100%. $^1$H NMR ($C_6D_6$): δ 7.61 (4H, s), 6.69 (4H, s), 3.99 (2H, s), 2.13 (12H, s), 2.07 (6H, s), 1.69 (6H, s), 1.32 (18H, s), 0.56 (12H, s).

Example 4

Synthesis of 4,6-bis(chlorodimethylsilyl)dibenzofuran (3)

The reaction outlined in the reaction scheme below is as follows: 4,6-Diiododibenzofuran was prepared from dibenzofuran by reaction with BuLi/TMEDA and iodine using a modification of a published procedure (Tsang, K. Y. and coworkers J. Am. Chem. Soc. 1994, 116, pages 3988-4005). Toluene (150 mL) was added to 4,6-diiododibenzofuran (7.01 g, 16.7 mmol) to form a clear yellow solution. This was cooled to −85° C. This caused a suspension to form. Then a hexane solution of BuLi (14.5 mL, 35.9 mmol) was added dropwise over a couple of minutes. The diiodide dissolved and a cloudy solution formed. After 45 minutes SiMe$_2$Cl$_2$ (18.5 g, 144 mmol), which had been cooled to −35° C., was added in one portion.

The mixture was allowed to warm slowly to ambient temperature over 4 h. The volatiles were then removed under reduced pressure and the yellow solid was extracted with Et$_2$O (80 mL) and filtered. Concentration to 25 mL and cooling to −35° C. afforded 2.90 g of the product identified as 3 in the reaction scheme as colorless crystals. An additional two crops of product were isolated from the mother liquor after further concentration and addition of hexane. Total yield: 4.51 g, 76.4%. $^1$H NMR (250 MHz, CDCl$_3$): δ 8.04 (2H, d), 7.69 (2H, d), 7.39 (2H, d), 0.87 (12H, s).

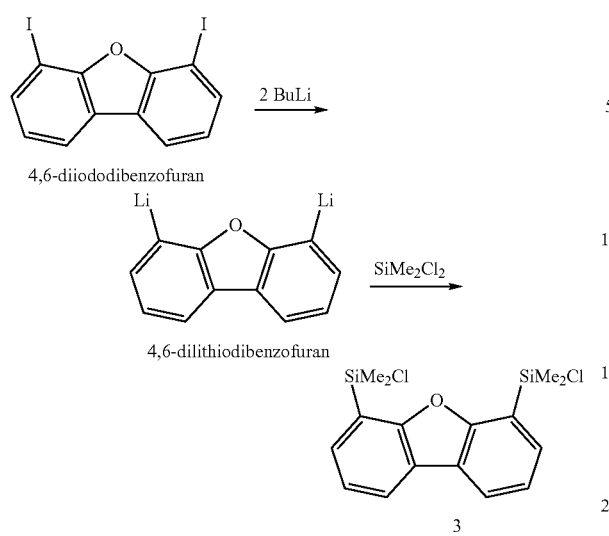

Example 5

Synthesis of [4a]L₂

The reaction outlined in the reaction scheme below is as follows: Toluene (15 mL) and tetrahydrofuran (0.5 mL) were added to 2,6-diisopropylanilidolithium (0.515 g, 2.81 mmol) to form a nearly clear, pale yellow solution. To this was added dropwise a toluene (5 mL) solution of the product identified as 3 in the reaction scheme (0.497 g, 1.41 mmol). After 30 min the volatiles were removed and the oily residue was extracted with hexane (10 mL).

The solution was filtered and the volatiles were removed to afford [4a]H₂ as a thick yellow oil (0.92 g, 100%). ¹H NMR (250 MHz, CDCl₃): δ 8.01 (2H, d), 7.62 (2H, d), 7.35 (2H, d), 7.00 (6H, br s), 3.28 (4H, sept), 1.00 (24H, d), 0.49 (12H, s).

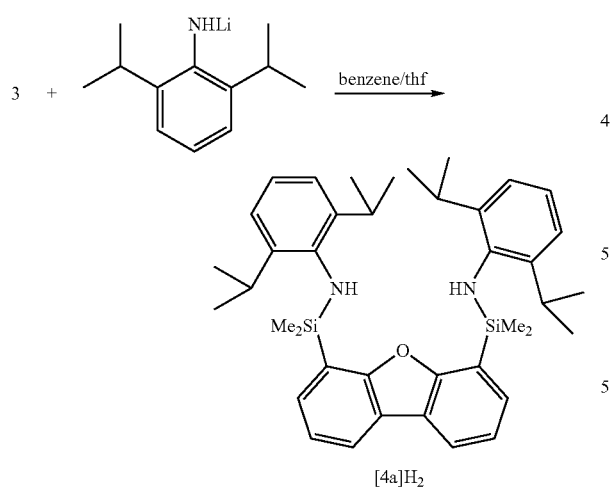

Example 6

Synthesis of [2b]HfCl₂

The reaction outlined in the reaction scheme below is as follows: Benzene (5 mL) was added to [2b]H₂ (0.696 g, 0.949 mmol) to form a clear colorless solution. Solid LiCH₂SiMe₃ (0.179 g, 1.90 mmol) was then added. After 15 min the volatiles were removed to afford an oil that crystallized upon the addition of hexane to give clean [2b]Li₂. Yield=0.375 g, 53.0%. ¹H NMR (250 MHz, C₆D₆): δ 7.66 (2H, d), 7.55 (2H, d), 6.93 (4H, d), 6.77 (2H, t), 2.50 (4H, m), 2.29 (4H, m), 1.65 (6H, s), 1.31 (18H, s), 0.92 (12H, t), 0.55 (12H, s).

Toluene (15 mL), [2b]Li₂ (0.187 g, 0.251 mmol), and HfCl₄ (0.080 g, 0.25 mmol) were combined in a Teflon-capped flask. The mixture was heated to 140° C. for 4 h. The volatiles were then removed and the residue was extracted with benzene (5 mL) and filtered. Removal of the volatiles afforded an oil that was crystallized from hexamethyldisiloxane (0.5 mL). Yield: 0.157 g, 63.8%. Due to fluxionality on the timescale of data acquisition several resonances in the ¹H NMR spectrum were broad. ¹H NMR (250 MHz, C₆D₆): δ 7.63 (2H, d), 7.50 (2H, d), 7.07 (6H, br), 3.45-2.45 (8H, v br), 1.79 (6H, br), 1.5-0.7 (30H, br overlapping), 0.03 (6H, br).

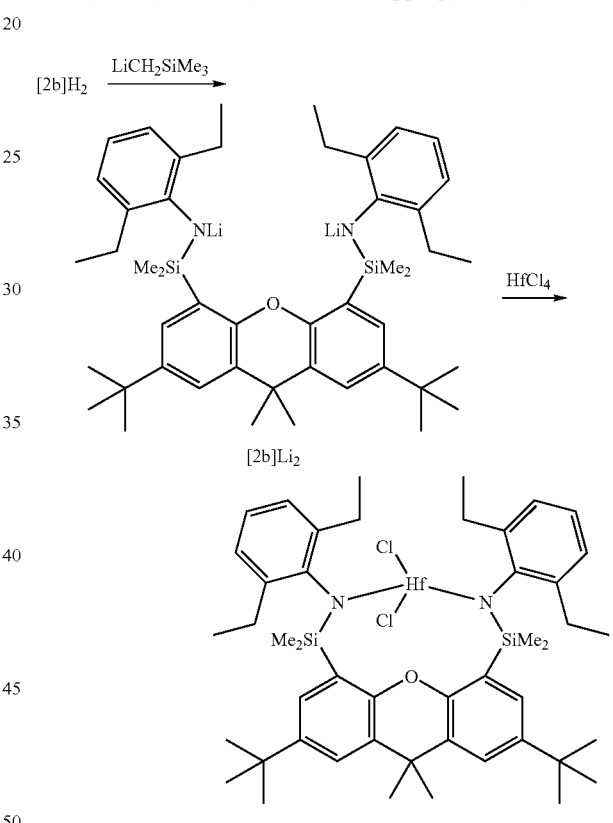

Example 7

Synthesis of [2c]HfCl₂

Benzene (15 mL) was added to [2c]H₂ (1.04 g, 1.48 mmol) to form a homogeneous solution. Then a benzene (5 mL) solution of LiCH₂SiMe₃ (0.279 g, 2.96 mmol) was added dropwise. After 30 min the solution was filtered and the volatiles were removed to afford [2c]Li₂ as a white solid. Yield: 1.06 g, 100%. ¹H NMR(C₆D₆): δ 7.67 (2H, d), 7.56 (2H, d), 6.68 (4H, s), 2.07 (6H, s), 1.92 (12H, s), 1.62 (6H, s), 1.33 (18H, s), 0.53 (12H, s)

Toluene (6 mL) was added to [2c]Li2 (0.198 g, 0.281 mmol) to form a clear colorless solution. Then HfCl₄ (0.090 g, 0.28 mmol) was added, and the mixture was heated to 100° C. for 3.5 h. The temperature was reduced to 80° C. and the mixture was stirred for 3 days. The volatiles were removed and the residue was extracted with $CH_2Cl_2$ (3 mL) and filtered. Removal of the volatiles under reduced pressure afforded [2c]$HfCl_2$ as a foamy semi solid. Yield: 0.257 g, 96.0%. $^1$H NMR($C_6D_6$): δ 7.64 (2H, d), 7.53 (2H, d), 6.78 (4H, br), 2.45 (12H, br), 2.11 (6H, s), 1.80 (6H, s), 1.30 (18H, s), 0.3 (12H, vbr).

Example 8

Synthesis of [2b]$HfMe_2$

Benzene (3 mL) was added to [2b]$HfCl_2$ (0.157 g, 0.160 mmol) to form a clear colorless solution. An $Et_2O$ solution of $Me_2Mg$ (1.00 mL, 0.168 mmol) was added dropwise. After 2 h the volatiles were removed and the residue was extracted with benzene. Filtration and removal of the volatiles afforded the product as a gummy off white solid. Yield: 0.13 g, 86%. Due to fluxionality on the timescale of data acquisition several resonances in the $^1$H NMR spectrum were extremely broad and undefined. $^1$H NMR (250 MHz, $C_6D_6$): δ 7.60 (4H, s), 7.14-7.00 (6H, m), 3.2-2.6 (8H, br), 1.76 (6H, s), 1.34 (18H, s), 1.20 (10H, br).

Example 9

Synthesis of [2a]$HfMe_2$

[2a]$HfMe_2$ was prepared analogously to [2b]$HfMe_2$, but using [2a]$Li_2$ in place [2b]$Li_2$. $^1$H NMR spectroscopic data indicates CS symmetry but the Me resonances are all broadened. $^1$H NMR (250 MHz, $C_6D_6$): δ 7.60 (2H, d), 7.58 (2H, d), 7.1-7.0 (6H, m), 3.92 (2H, m), 3.86 (2H, m), 1.75 (3H, s), 1.64 (3H, s), 1.45-1.22 (33H, overlapping), 1.02 (3H, s), 0.99 (3H, s), 0.92 (9H, overlapping), 0.31 (3H, s), 0.21 (6H, s), −0.01 (3H, s). FIG. 1 shows the molecular structure of [2a]$HfMe_2$ drawn with 50% thermal ellipsoids.

Example 10

Synthesis of [2c]$HfMe_2$

Benzene (6 mL) was added to [2c]$HfCl_2$ (0.240 g, 0.252 mmol) to form a colorless solution. An $Et_2O$ solution of $Me_2Mg$ (1.73 mL, 0.265 mmol) was added dropwise. After 1 hour the volatiles were removed to afford and oily residue. The residue was extracted with hexane (8 mL) and filtered. Removal of the volatiles afforded [2c]$HfMe_2$ as a foamy semi solid. Yield: 0.204 g, 88.8%. $^1$H NMR ($C_6D_6$): δ 7.62 (4H, m), 6.79 (4H, s), 2.34 (12H, s), 2.08 (6H, s), 1.77 (6H, s), 1.35 (18H, s), 0.58 (6H, br), −0.17 (6H, br).

Example 11

Synthesis of [2e]$HfBn_2$

The reaction outlined in the reaction scheme below is as follows: Toluene (4 mL) was added to [2e]$H_2$ (87 mg, 0.13 mmol) and $HfBn_4$ (70 mg, 0.13 mmol). The mixture was shielded from light and heated to 100° C. for 60 min. The volatiles were removed to afford [2e]$HfBn_2$ as an oil (135 mg, 100%). The oil was later crystallized from hexamethyl disiloxane (2 mL) at ambient temperature. $^1$H NMR (250 MHz, $C_6D_6$): δ 7.59 (4H, d), 6.87 (4H, d), 6.58 (2H, br s), 6.52 (4H, br s), 2.00 (12H, s), 1.81 (4H, s), 1.69 (6H, s), 1.28 (18H, s), 0.66 (12H, s).

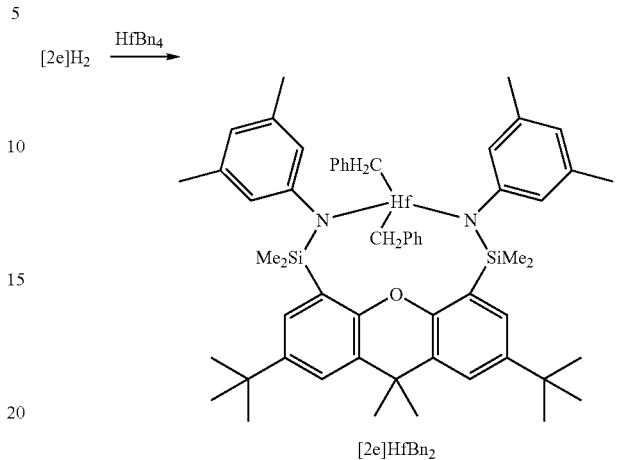

Example 12

Synthesis of [4a]$Li_2$

A hexane (4 mL) solution of $LiCH_2SiMe_3$ (0.144 g, 1.53 mmol) was added dropwise to a hexane (4 mL) solution of [4a]$H_2$ (0.486 g, 0.765 mmol). After the addition a white precipitate formed. After 15 min the solution was concentrated to 5 mL and the white solid was collected on a fritted disk and dried under reduced pressure (0.299 g). The mother liquor was concentrated to 2.5 mL and left at ambient temperature. The next day a second crop of [4a]$Li_2$ was isolated as pale pink crystals (70 mg). Total yield: 0.369 g, 74.4%. [4a]$Li_2$. Yield=0.375 g, 53.0%. $^1$H NMR (250 MHz, $C_6D_6$): δ 7.71 (2H, d), 7.53 (2H, d), 7.26 (2H, t), 6.89 (4H, d), 6.65 (2H, t), 3.33 (4H, sept), 0.99 (12H, d), 0.87 (12H, d), 0.45 (12H, s).

Example 13

Synthesis of [4a]$ZrCl_2$

Figure 2:
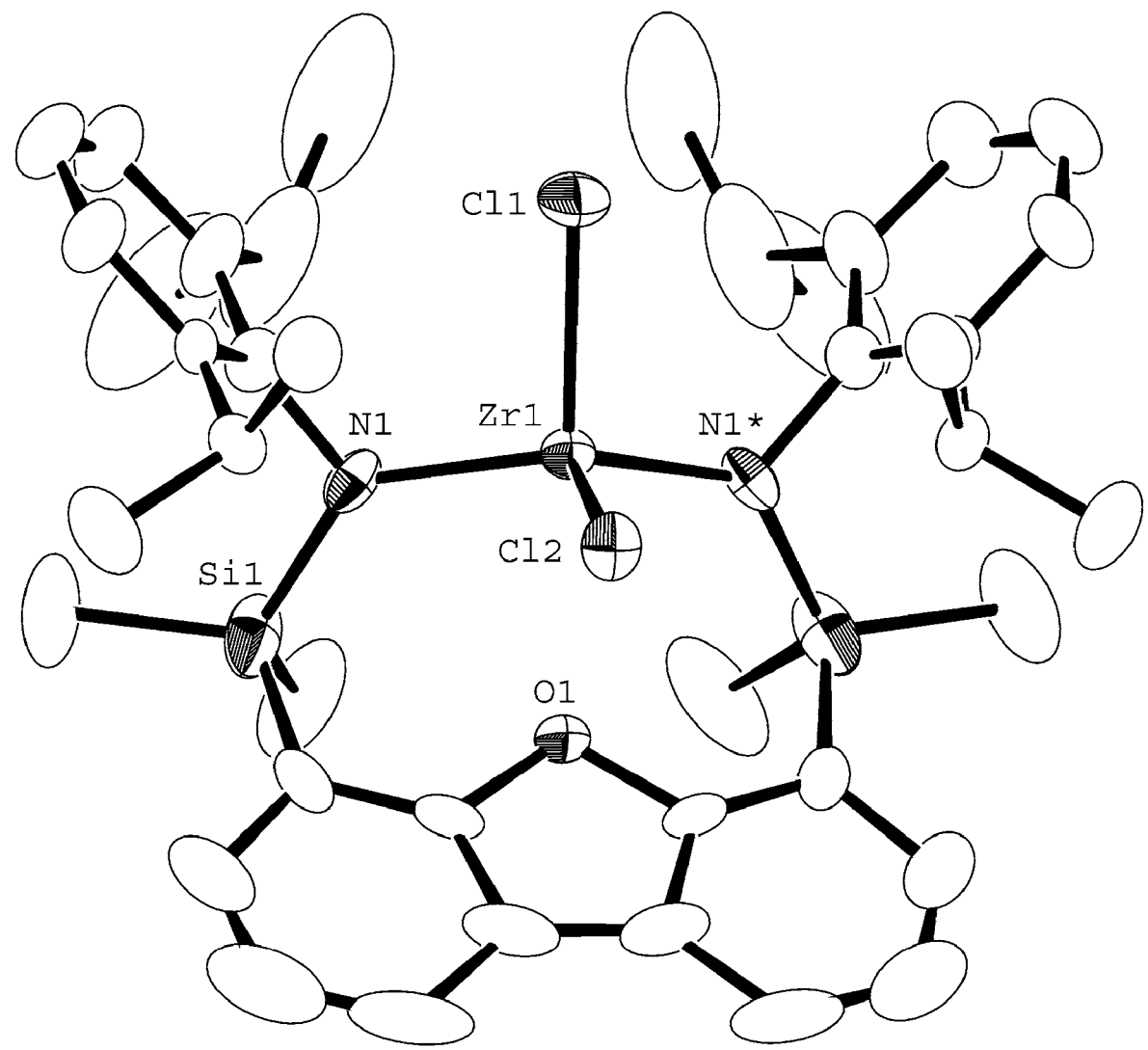
FIG. 2 is an illustration of the molecular structure of a [4a]$ZrCl_2$ compound drawn with 50% thermal ellipsoids as determined by single-crystal X-ray diffraction.

Toluene (6 mL) was added to $ZrCl_4$ (27 mg, 0.12 mmol) to form a colorless suspension. To this was added dropwise a toluene (6 mL) solution of [4a]$Li_2$ (63 mg, 0.097 mmol). The reaction was heated to 60° C. for 3 h and then the volatiles were removed under reduced pressure. The residue was extracted with $Et_2O$ (5 mL) and filtered. The solution was concentrated to 2 mL and left overnight. The [4a]$ZrCl_2$ was isolated as colorless crystals (35 mg, 45%). $^1$H NMR (250 MHz, $C_6D_6$): δ 7.61 (2H, d), 7.33 (2H, d), 7.18 (2H, d), 7.07 (6H, s), 3.63 (4H, br sept), 1.36 (12H, d), 1.15 (12H, d), 0.43 (12, br s). The molecular structure of [4a]$ZrCl_2$ drawn with 50% thermal ellipsoids is shown in FIG. 2.

Example 14

Reactivity of Activated Complexes with Alkenes

Diamido transition metal complexes of the diamine ligand precursors, when mixed with appropriate activators, were found to react with ethylene-octene mixtures to form oligomers and polymers. Selected results are shown in the follow ing table. In some cases highly active catalysts were formed. Specific reaction conditions for each entry are presented in the following table. Details of the experiment and product characterization are presented after the table. Activities are reported as grams of polymer/mmol of catalyst/hour/bar of ethylene pressure. Abbreviations used in the table: nmol is nanomoles, dmah-NCA is N,N-dimethylanilinium tetrakis (pentafluorophenyl)borate, MAO is methyl alumoxane.

| Ex. | Catalyst | Activator | Temp (° C.) | Activity | Octene (wt %) | Mw | Mn | Mw/Mn |
|---|---|---|---|---|---|---|---|---|
| 1 | [2a]HfMe$_2$ | dmah-NCA | 50 | 18 | — | — | — | — |
| 2 | [2a]HfMe$_2$ | dmah-NCA | 80 | 4 | — | — | — | — |
| 3 | [2a]HfMe$_2$ | MAO | 50 | 22 | 0 | 743,674 | 401,998 | 1.8 |
| 4 | [2a]HfMe$_2$ | MAO | 80 | 14 | — | — | — | — |
| 5 | [2a]ZrMe$_2$ | dmah-NCA | 50 | 102 | 1 | 2,586,984 | 1,341,496 | 1.9 |
| 6 | [2a]ZrMe$_2$ | dmah-NCA | 80 | 17 | — | — | — | — |
| 7 | [2a]ZrMe$_2$ | MAO | 50 | 212 | 1 | 1,725,695 | 996,627 | 1.7 |
| 8 | [2a]ZrMe$_2$ | MAO | 80 | 25 | 1 | 342,989 | 208,170 | 1.6 |
| 9 | [2b]HfMe$_2$ | dmah-NCA | 50 | 3519 | 1 | 4,044,823 | 2,845,910 | 1.4 |
| 10 | [2b]HfMe$_2$ | dmah-NCA | 70 | 2885 | 1 | 2,953,787 | 1,963,826 | 1.5 |
| 11 | [2b]HfMe$_2$ | dmah-NCA | 80 | 1889 | 2 | 2,339,306 | 1,439,365 | 1.6 |
| 12 | [2b]HfMe$_2$ | dmah-NCA | 90 | 261 | 0 | 1,705,957 | 467,010 | 3.7 |
| 13 | [2b]HfMe$_2$ | dmah-NCA | 110 | 35 | 1 | 672,492 | 408,099 | 1.6 |
| 14 | [2b]HfMe$_2$ | MAO | 50 | 1803 | 1 | 231,888 | 147,655 | 1.6 |
| 15 | [2b]HfMe$_2$ | MAO | 70 | 1672 | 1 | 183,406 | 127,050 | 1.4 |
| 16 | [2b]HfMe$_2$ | MAO | 80 | 943 | 1 | 172,477 | 115,559 | 1.5 |
| 17 | [2b]HfMe$_2$ | MAO | 90 | 648 | 0 | 132,933 | 91,217 | 1.5 |
| 18 | [2b]HfMe$_2$ | MAO | 110 | 35 | 1 | 61,298 | 24,621 | 2.5 |
| 19 | [2b]ZrMe$_2$ | dmah-NCA | 50 | 201 | 1 | 1,342,823 | 809,117 | 1.7 |
| 20 | [2b]ZrMe$_2$ | dmah-NCA | 80 | 16 | — | — | — | — |
| 21 | [2b]ZrMe$_2$ | MAO | 50 | 424 | 1 | 634,407 | 385,278 | 1.6 |
| 22 | [2b]ZrMe$_2$ | MAO | 80 | 22 | 1 | 229,304 | 130,439 | 1.8 |
| 23 | [2c]HfMe$_2$ | dmah-NCA | 50 | 1673 | 1 | 3,361,219 | 2,176,169 | 1.5 |
| 24 | [2c]HfMe$_2$ | dmah-NCA | 80 | 116 | 1 | 1,652,418 | 1,024,693 | 1.6 |
| 25 | [2c]HfMe$_2$ | MAO | 50 | 920 | 1 | 101,465 | 59,272 | 1.7 |
| 26 | [2c]HfMe$_2$ | MAO | 80 | 62 | 0 | 68,516 | 44,139 | 1.6 |
| 27 | [2c]ZrMe$_2$ | dmah-NCA | 50 | 31 | 0 | 1,154,420 | 667,095 | 1.7 |
| 28 | [2c]ZrMe$_2$ | dmah-NCA | 80 | 6 | — | — | — | — |
| 29 | [2c]ZrMe$_2$ | MAO | 50 | 33 | 0 | 263,588 | 176,076 | 1.5 |
| 30 | [2c]ZrMe$_2$ | MAO | 80 | 15 | — | — | — | — |
| 31 | [2e]HfBn$_2$ | dmah-NCA | 50 | 468 | 2 | 102,331 | 59,763 | 1.7 |
| 32 | [2e]HfBn$_2$ | dmah-NCA | 70 | 915 | — | 91237 | 53780 | 1.7 |
| 33 | [2e]HfBn$_2$ | dmah-NCA | 80 | 981 | 1 | 100,073 | 69,883 | 1.4 |
| 34 | [2e]HfBn$_2$ | dmah-NCA | 90 | 1211 | — | 90956 | 57299 | 1.6 |
| 35 | [2e]HfBn$_2$ | dmah-NCA | 110 | 893 | — | 72215 | 43629 | 1.7 |
| 36 | [2e]HfBn$_2$ | MAO | 50 | 127 | 5 | 4,589 | 3,706 | 1.2 |
| 37 | [2e]HfBn$_2$ | MAO | 70 | 239 | — | 7378 | 5197 | 1.4 |
| 38 | [2e]HfBn$_2$ | MAO | 80 | 229 | 4 | 7,887 | 6,052 | 1.3 |
| 39 | [2e]HfBn$_2$ | MAO | 90 | 210 | — | 5880 | 4155 | 1.4 |
| 40 | [2e]HfBn$_2$ | MAO | 110 | 95 | — | 3797 | 2802 | 1.4 |
| 41 | [2f]HfMe$_2$ | dmah-NCA | 50 | 208 | 1 | 386,284 | 157,084 | 2.5 |
| 42 | [2f]HfMe$_2$ | dmah-NCA | 80 | 1075 | 3 | 282,647 | 153,318 | 1.8 |
| 43 | [2f]HfMe$_2$ | MAO | 50 | 219 | 4 | 13,994 | 4,424 | 3.2 |
| 44 | [2f]HfMe$_2$ | MAO | 80 | 411 | 2 | 13,791 | 6,445 | 2.1 |
| 45 | [4a]ZrCl$_2$ | dmah-NCA | 50 | 2 | — | — | — | — |
| 46 | [4a]ZrCl$_2$ | dmah-NCA | 80 | 0 | — | — | — | — |
| 47 | [4a]ZrCl$_2$ | MAO | 50 | 14 | — | — | — | — |

-continued

| Ex. | Catalyst | Activator | Temp (° C.) | Activity | Octene (wt %) | Mw | Mn | Mw/Mn |
|---|---|---|---|---|---|---|---|---|
| 48 | [4a]ZrCl$_2$ | MAO | 80 | 27 | — | — | — | — |
| 49 | [4a]ZrMe$_2$ | dmah-NCA | 50 | 0 | — | — | — | — |
| 50 | [4a]ZrMe$_2$ | dmah-NCA | 80 | 0 | — | — | — | — |
| 51 | [4a]ZrMe$_2$ | MAO | 50 | 5 | — | — | — | — |
| 52 | [4a]ZrMe$_2$ | MAO | 80 | 7 | — | — | — | — |

Activity is given in g/mmol/h/bar).
Mw, Mn and Mw/Mn values are determined by GPC.

Ethylene/1-octene copolymerizations were carried out in a parallel pressure reactor, which is described in U.S. Pat. Nos. 6,306,658; 6,455,316; and 6,489,1681; WO 00/09255; and Murphy et al., J. Am. Chem. Soc., 2003, 125, pages 4306-4317, each of which is fully incorporated herein by reference. A pre-weighed glass vial insert and disposable stirring paddle were fitted to each reaction vessel of the reactor, which contains 48 individual reaction vessels. The reactor was then closed and each vessel was individually heated to a set temperature (usually between 50 and 110° C.) and pressurized to a pre-determined pressure of 1.38 MPa (200 psi) ethylene. 1-Octene (100 microliters, 637 micromol) was injected into each reaction vessel through a valve, followed by enough toluene to bring the total reaction volume, including the subsequent additions, to 5 mL. Tri-n-octylaluminum in toluene (100 microliters, 10 mM in toluene, 1 micromol) was then added to act as a co-catalyst/scavenger.

The contents of the vessel were then stirred at 800 rpm. An activator solution (either 1.0 equiv of 0.40 mM dmah-NCA in toluene or 400 equiv of 1 wt % MAO in toluene) was then injected into the reaction vessel along with 500 microliters toluene, followed by a toluene solution of catalyst (0.40 mM in toluene, 80 nmols of catalyst in all cases except for entries 45-48 which used 40 nmols of catalyst) and another aliquot of toluene (500 microliters). The reaction was then allowed to proceed until a set time limit (usually 30 min) or until a set amount of ethylene had been taken up by the reaction (ethylene pressure was maintained in each reaction vessel at the pre-set level by computer control). At this point, the reaction was quenched by pressurizing the vessel with compressed air. After the polymerization reaction, the glass vial insert containing the polymer product and solvent was removed from the pressure cell and the inert atmosphere glovebox, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight, by FT-IR (see below) to determine comonomer incorporation, and by DSC (see below) to determine melting point.

To determine various molecular weight related values by GPC, high temperature size exclusion chromatography was performed using an automated "Rapid GPC" system as described in U.S. Pat. Nos. 6,491,816; 6,491,823; 6,475,391; 6,461,515; 6,436,292; 6,406,632; 6,175,409; 6,454,947; 6,260,407; and 6,294,388; each of which is fully incorporated herein by reference for US purposes. This apparatus has a series of three 30 cm×7.5 mm linear columns, each containing PLgel 10 um, Mix B. The GPC system was calibrated using polystyrene standards ranging from 580-3,390,000 g/mol. The system was operated at an eluent flow rate of 2.0 mL/min and an oven temperature of 165° C. 1,2,4-trichlorobenzene was used as the eluent. The polymer samples were dissolved in 1,2,4-trichlorobenzene at a concentration of 0.1-0.9 mg/mL. 250 uL of a polymer solution were injected into the system. The concentration of the polymer in the eluent was monitored using an evaporative light scattering detector. The molecular weights presented are relative to linear polystyrene standards.

Differential Scanning Calorimetry (DSC) measurements were performed on a TA-Q100 instrument to determine the melting point of the polymers. Samples were pre-annealed at 220° C. for 15 minutes and then allowed to cool to room temperature overnight. The samples were then heated to 220° C. at a rate of 100° C./min and then cooled at a rate of 50° C./min. Melting points were collected during the heating period.

The ratio of 1-octene to ethylene incorporated in the polymers (weight %) was determined by rapid FT-IR spectroscopy on a Bruker Equinox 55+ IR in reflection mode. Samples were prepared in a thin film format by evaporative deposition techniques. Weight percent 1-octene was obtained from the ratio of peak heights at 1378 and 4322 cm$^{-1}$. This method was calibrated using a set of ethylene/1-octene copolymers with a range of known wt % 1-octene content.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law.

What is claimed is:

1. A transition metal complex of the general formula (III):

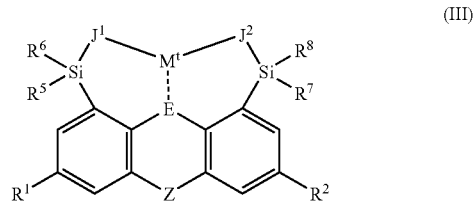

(III)

wherein M$^r$ is a group 3 to 12 element in a +2 to +6 oxidation state with between 1 to 4 additional ligands (anionic and/or neutral) coordinated, wherein R$^1$ and R$^2$ are hydrogen, halogen, alkoxy, or a hydrocarbon group containing between 1 to 12 carbon atoms; E is a group 16 element; Z is a direct bond between carbon atoms of the adjacent aromatic rings or a —CR³R⁴— or —SiR³R⁴— bridge between those carbon atoms, where R³ and R⁴ are hydrogen or a hydrocarbon groups with 1 to 10 carbons, R⁵, R⁶, R⁷ and R⁸ are hydrogen, halogen, alkoxy, or a hydrocarbon group containing between 1 to 10 carbon atoms and J¹ and J² are —NR⁹R¹⁰ or —PR⁹R¹⁰, where R⁹ is H or SiMe₃ group and R¹⁰ is selected from the group consisting of alkyl, aryl, substituted aryl, heteroalkyl, and heteroaryl containing between 1 to 30 non-hydrogen atoms.

2. The transition metal complex of claim 1 in which the two amine functionalities of the diamine ligand precursor are joined by a tricyclic linker that may be either a 4,5-disubstituted 9,9-dimethylxanthene or a 4,6-disubstituted dibenzofuran.

3. The transition metal complex of claim 1 in which R¹⁰ is an aryl moiety substituted in the ortho positions.

4. The transition metal complex of claim 1 in which R¹⁰ contains 2,6-diethylphenyl moieties.

5. A process to produce a transition metal complex comprising:
  1) coupling a 4,5-dilithioxanthene derivative or a 4,6-dilithiodibenzofuran derivative with a dihalosilane and producing a compound represented by the formula (I):

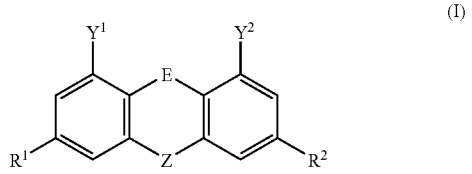

wherein R¹ and R² are hydrogen, halogen, alkoxy or a hydrocarbon group containing between 1 to 10 carbon atoms; E is O; Z is a direct bond between carbon atoms of the adjacent aromatic rings or a —CR³R⁴— bridge between those carbon atoms, where R³ and R⁴ are hydrogen or a hydrocarbon groups with 1 to 10 carbons, and Y¹ and Y² are reactive halosilyl groups; thereafter
  2) reacting the compound represented by the formula (I) with an amine or a group 1 or 2 metal amide to form a ligand precursor compound represented by the formula (II):

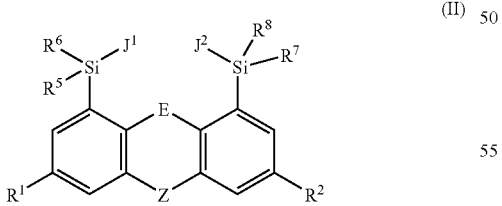

wherein R¹ and R² are hydrogen, halogen, alkoxy, or a hydrocarbon group containing between 1 to 10 carbon atoms; E is a group 16 element; Z is a direct bond between carbon atoms of the adjacent aromatic rings or a —CR³R⁴— or —SiR³R⁴— bridge between those carbon atoms, where R³ and R⁴ are hydrogen or a hydrocarbon groups with 1 to 10 carbons, R⁵, R⁶, R⁷ and R⁸ are hydrogen, halogen, alkoxy or a hydrocarbon group containing between 1 to 12 carbon atoms and J¹ and J² are —NR⁹R¹⁰ or —PR⁹R¹⁰, where R⁹ is a H or SiMe₃ group and R¹⁰ is selected from a group consisting of alkyl, aryl, substituted aryl, heteroalkyl, and heteroaryl containing between 1 to 30 non-hydrogen atoms; thereafter 3) subjecting the compound represented by the formula (II) to deprotonation by a group 1 or 2 organometallic base followed by reaction of the generated metal amide with a transition metal halide to produce a transition metal complex.

6. A transition metal complex of the general formula (III):

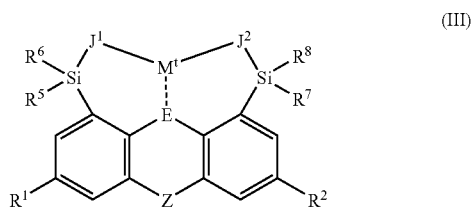

wherein M' is a group 3 to 12 element in a +2 to +6 oxidation state with between 1 to 4 additional ligands (anionic and/or neutral) coordinated, wherein R¹ and R² are hydrogen, halogen, alkoxy, or a hydrocarbon group containing between 1 to 12 carbon atoms; E is a group 16 element; Z is a direct bond between carbon atoms of the adjacent aromatic rings or a —CR³R⁴— or —SiR³R⁴— bridge between those carbon atoms, where R³ and R⁴ are hydrogen or a hydrocarbon groups with 1 to 10 carbons, R⁵, R⁶, R⁷ and R⁸ are hydrogen, halogen, alkoxy or a hydrocarbon group containing between 1 to 10 carbon atoms and J¹ and J² are N-iPr, N-(2,4,6-(CH₃)₃ phenyl), N-(m-(tBu)₂ phenyl), N-(o-(ethyl)₂ phenyl), or N-(o-(isopropyl)₂ phenyl).

7. A transition metal complex represented by the formula:

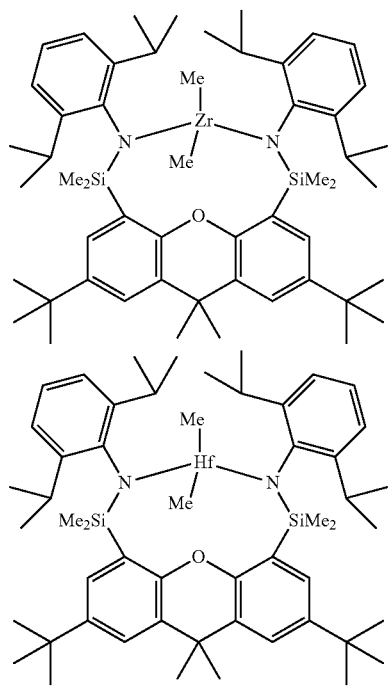

-continued
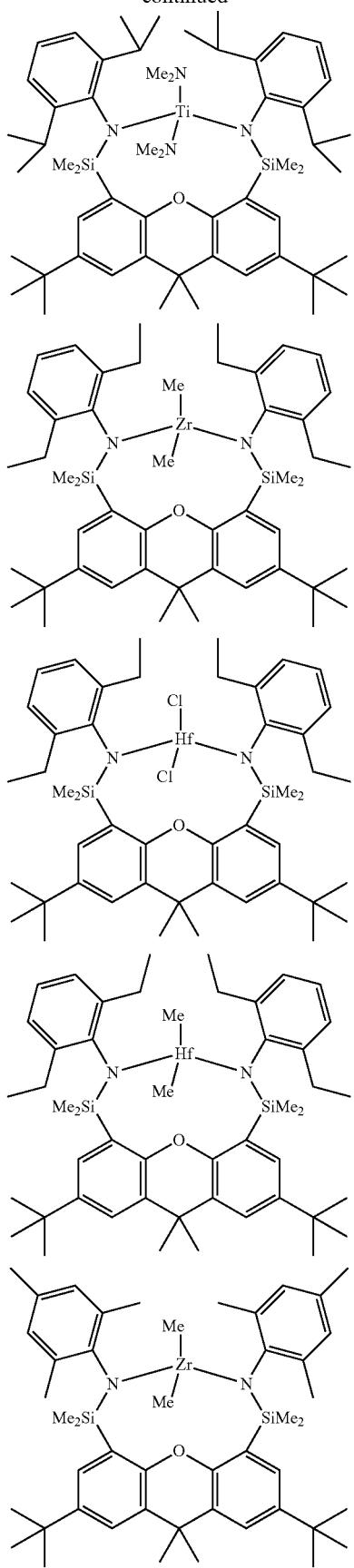
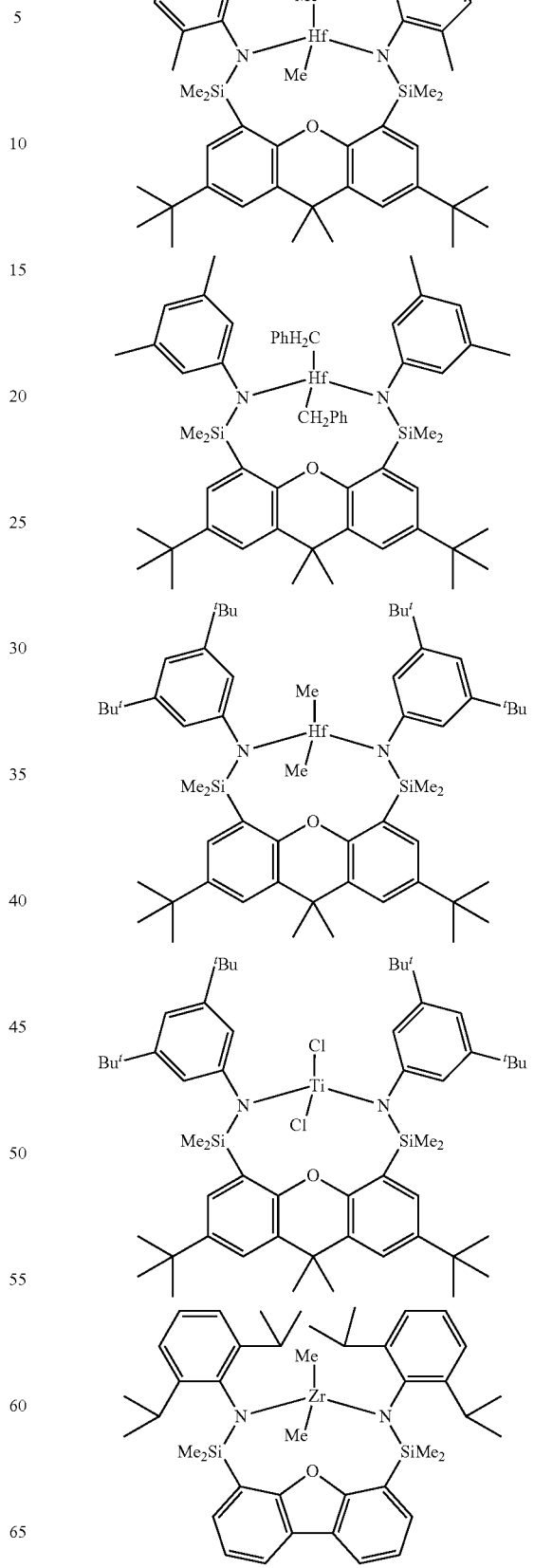

-continued

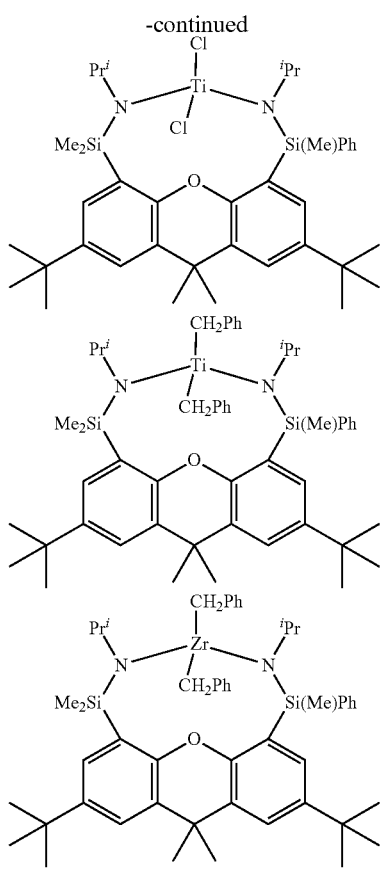

where Me is methyl, Ph is phenyl, $^i$Pr is isopropyl, and $^t$Bu is t-butyl and Bn is benzyl.

8. A process to produce a transition metal complex comprising:
1) coupling a 4,5-dilithioxanthene derivative or a 4,6-dilithiodibenzofuran derivative with a dihalosilane and producing a compound represented by the formula (I):

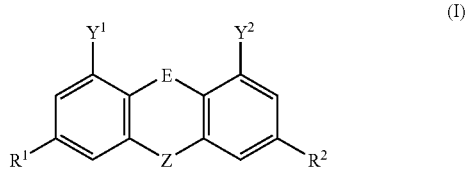

wherein $R^1$ and $R^2$ are hydrogen, halogen, alkoxy or a hydrocarbon group containing between 1 to 10 carbon atoms; E is O; Z is a direct bond between carbon atoms of the adjacent aromatic rings or a —$CR^3R^4$— bridge between those carbon atoms, where $R^3$ and $R^4$ are hydrogen or a hydrocarbon groups with 1 to 10 carbons, and $Y^1$ and $Y^2$ are reactive halosilyl groups; thereafter
2) reacting the compound represented by the formula (I) with an amine or a group 1 or 2 metal amide to form a ligand precursor compound represented by the formula (II):

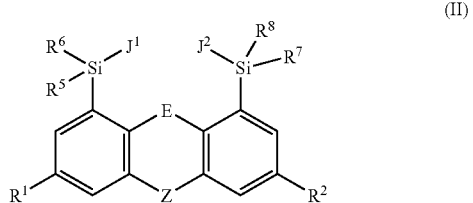

wherein $R^1$ and $R^2$ are hydrogen, halogen, alkoxy, or a hydrocarbon group containing between 1 to 10 carbon atoms; E is a group 16 element; Z is a direct bond between carbon atoms of the adjacent aromatic rings or a —$CR^3R^4$— or —$SiR^3R^4$— bridge between those carbon atoms, where $R^3$ and $R^4$ are hydrogen or a hydrocarbon groups with 1 to 10 carbons, $R^5$, $R^6$, $R^7$ and $R^8$ are hydrogen, halogen, alkoxy or a hydrocarbon group containing between 1 to 12 carbon atoms and $J^1$ and $J^2$ are —$NR^9R^{10}$ or —$PR^9R^{10}$, where $R^9$ is a H group and $R^{10}$ is selected from a group consisting of alkyl, aryl, substituted aryl, heteroalkyl, and heteroaryl containing between 1 to 30 non-hydrogen atoms; thereafter 3) subjecting the compound represented by the formula (II) to deprotonation by a group 1 or 2 organometallic base followed by reaction of the generated metal amide with a transition metal halide to produce a transition metal complex in a salt-metathesis reaction.

9. A process to produce a transition metal complex comprising:
1) coupling a 4,5-dilithioxanthene derivative or a 4,6-dilithiodibenzofuran derivative with a dihalosilane and producing a compound represented by the formula (I):

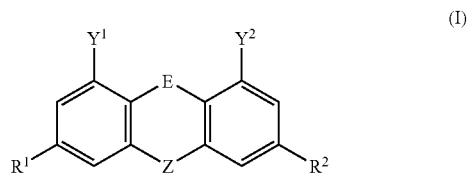

wherein $R^1$ and $R^2$ are hydrogen, halogen, alkoxy or a hydrocarbon group containing between 1 to 10 carbon atoms; E is O; Z is a direct bond between carbon atoms of the adjacent aromatic rings or a —$CR^3R^4$— bridge between those carbon atoms, where $R^3$ and $R^4$ are hydrogen or a hydrocarbon groups with 1 to 10 carbons, and $Y^1$ and $Y^2$ are reactive halosilyl groups; thereafter
2) reacting the compound represented by the formula (I) with an amine or a group 1 or 2 metal amide to form a ligand precursor compound represented by the formula (II):

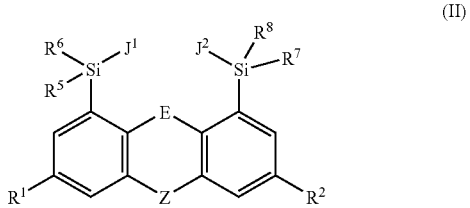

wherein $R^1$ and $R^2$ are hydrogen, halogen, alkoxy, or a hydrocarbon group containing between 1 to 10 carbon atoms; E is a group 16 element; Z is a direct bond between carbon atoms of the adjacent aromatic rings or a —$CR^3R^4$— or —$SiR^3R^4$— bridge between those carbon atoms, where $R^3$ and $R^4$ are hydrogen or a hydrocarbon groups with 1 to 10 carbons, $R^5$, $R^6$, $R^7$ and $R^8$ are hydrogen, halogen, alkoxy or a hydrocarbon group containing between 1 to 12 carbon atoms and $J^1$ and $J^2$ are —$NR^9R^{10}$ or —$PR^9R^{10}$, where $R^9$ is a H group and $R^{10}$ is selected from a group consisting of alkyl, aryl, substituted aryl, heteroalkyl, and heteroaryl containing between 1 to 30 non-hydrogen atoms; thereafter 3) subjecting the diamine ligand precursor represented by formula (II) to a reaction with an organometallic or metal(amido) reagent to form a transition metal diamdo complex in a protonolysis reaction.

10. A process to produce a transition metal complex comprising:
   1) coupling a 4,5-dilithioxanthene derivative or a 4,6-dilithiodibenzofuran derivative with a dihalosilane and producing a compound represented by the formula (I):

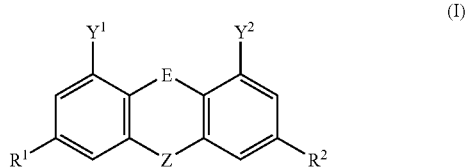

wherein $R^1$ and $R^2$ are hydrogen, halogen, alkoxy or a hydrocarbon group containing between 1 to 10 carbon atoms; E is O; Z is a direct bond between carbon atoms of the adjacent aromatic rings or a —$CR^3R^4$— bridge between those carbon atoms, where $R^3$ and $R^4$ are hydrogen or a hydrocarbon groups with 1 to 10 carbons, and $Y^1$ and $Y^2$ are reactive halosilyl groups; thereafter 2) reacting the compound represented by the formula (I) with an amine or a group 1 or 2 metal amide to form a ligand precursor compound represented by the formula (II):

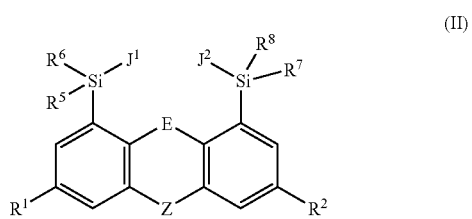

wherein $R^1$ and $R^2$ are hydrogen, halogen, alkoxy, or a hydrocarbon group containing between 1 to 10 carbon atoms; E is a group 16 element; Z is a direct bond between carbon atoms of the adjacent aromatic rings or a —$CR^3R^4$— or —$SiR^3R^4$— bridge between those carbon atoms, where $R^3$ and $R^4$ are hydrogen or a hydrocarbon groups with 1 to 10 carbons, $R^5$, $R^6$, $R^7$ and $R^8$ are hydrogen, halogen, alkoxy or a hydrocarbon group containing between 1 to 12 carbon atoms and $J^1$ and $J^2$ are —$NR^9R^{10}$ or —$PR^9R^{10}$, where $R^9$ is a $SiMe_3$ group and $R^{10}$ is selected from a group consisting of alkyl, aryl, substituted aryl, heteroalkyl, and heteroaryl containing between 1 to 30 non-hydrogen atoms; thereafter 3) subjecting the silylated diamine represented by the formula (II) to a reaction of with a metal halide to form a diamido complex.

11. The transition metal complex of claim 1 in which $R^{10}$ is a 2,6-disubstituted aryl moiety.

\* \* \* \* \*